US010575947B2

(12) United States Patent
Straubinger et al.

(10) Patent No.: US 10,575,947 B2
(45) Date of Patent: Mar. 3, 2020

(54) STENT FOR THE POSITIONING AND ANCHORING OF A VALVULAR PROSTHESIS IN AN IMPLANTATION SITE IN THE HEART OF A PATIENT

(71) Applicant: JenaValve Technology, Inc., Irvine, CA (US)

(72) Inventors: Helmut Straubinger, Aschheim (DE); Johannes Jung, Karlsruhe (DE)

(73) Assignee: JenaValve Technology, Inc., Irvine, CA (US)

( * ) Notice: Subject to any disclaimer, the term of this patent is extended or adjusted under 35 U.S.C. 154(b) by 98 days.

(21) Appl. No.: 15/850,165

(22) Filed: Dec. 21, 2017

(65) Prior Publication Data

US 2018/0360601 A1 Dec. 20, 2018

Related U.S. Application Data

(63) Continuation of application No. 14/709,909, filed on May 12, 2015, now Pat. No. 9,877,828, which is a
(Continued)

(51) Int. Cl.
*A61F 2/24* (2006.01)
(52) U.S. Cl.
CPC .... *A61F 2/2418* (2013.01); *A61F 2220/0016* (2013.01); *A61F 2230/0023* (2013.01); *A61F 2230/0054* (2013.01)
(58) Field of Classification Search
CPC ...... A61F 2220/0016; A61F 2230/0023; A61F 2230/0054; A61F 2/2418
See application file for complete search history.

(56) References Cited

U.S. PATENT DOCUMENTS

| 4,922,905 A | 5/1990 | Strecker |
| 5,002,566 A | 3/1991 | Carpentier et al. |
(Continued)

FOREIGN PATENT DOCUMENTS

| AU | 2006308187 A1 | 5/2007 |
| AU | 2006310681 A1 | 5/2007 |
(Continued)

OTHER PUBLICATIONS

Aortenklappenbioprothese erfolgreich in der Entwicklung, May 16, 2003 (1 page).
(Continued)

*Primary Examiner* — Julian W Woo
(74) *Attorney, Agent, or Firm* — Bookoff McAndrews, PLLC

(57) ABSTRACT

The present invention relates to a stent (10) for the positioning and anchoring of a valvular prosthesis (100) in an implantation site in the heart of a patient. Specifically, the present invention relates to an expandable stent for an endoprosthesis used in the treatment of a narrowing of a cardiac valve and/or a cardiac valve insufficiency. So as to ensure that no longitudinal displacement of a valvular prosthesis (100) fastened to a stent (10) will occur relative the stent (10) in the implanted state of the stent (10), even given the peristaltic motion of the heart, the stent (10) according to the invention comprises at least one fastening portion (11) via which the valvular prosthesis (100) is connectable to the stent (10). The stent (10) further comprises positioning arches (15) and retaining arches (16), whereby at least one positioning arch (15) is connected to at least one retaining arch (16) via a first connecting land (17). The stent (10) moreover comprises at least one auxiliary retaining arch (18) which connects the respective arms (16', 16") of the at least
(Continued)

Figure 1A:
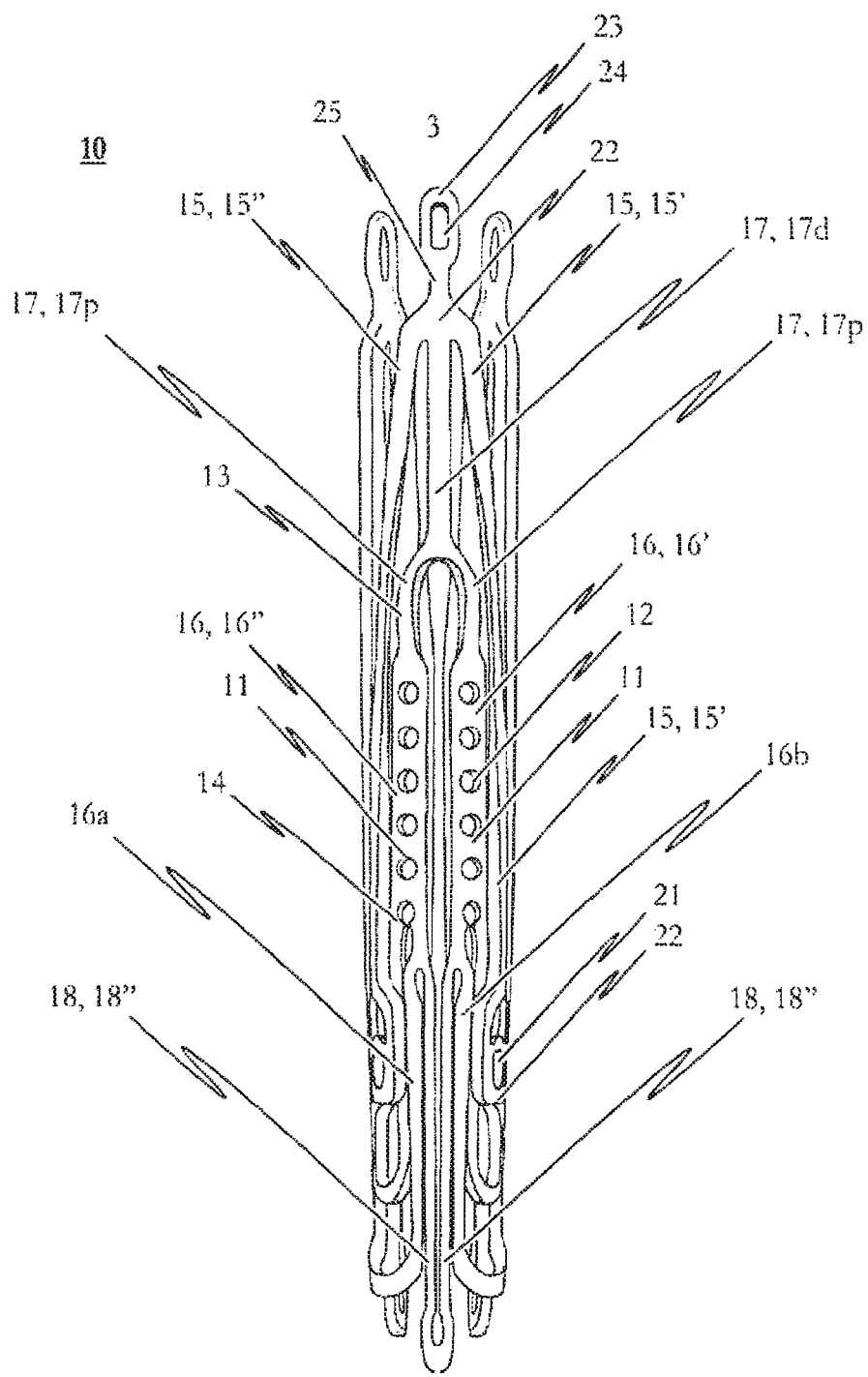

one retaining arch (16) connected to the at least one positioning arch (15).

21 Claims, 11 Drawing Sheets

Related U.S. Application Data continuation of application No. 12/071,814, filed on Feb. 26, 2008, now Pat. No. 9,044,318.

(56) References Cited

U.S. PATENT DOCUMENTS

| | | |
|---|---|---|
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,469,868 A | 11/1995 | Reger |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,101,396 B2 | 9/2006 | Artof et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,896,915 B2 | 3/2011 | Guyenot et al. |
| 7,914,575 B2 | 3/2011 | Guyenot et al. |
| 2001/0011187 A1 | 8/2001 | Pavcnik et al. |
| 2001/0039450 A1 | 11/2001 | Pavcnik et al. |
| 2002/0010489 A1 | 1/2002 | Gayzel et al. |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |

(56) References Cited

U.S. PATENT DOCUMENTS

| | | |
|---|---|---|
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137682 A1 | 6/2005 | Justino |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0255660 A1 | 10/2008 | Guyenot et al. |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0216312 A1 | 8/2009 | Straubinger et al. |
| 2009/0222076 A1 | 9/2009 | Figulla et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| EP | 0084395 A1 | 7/1983 |
| EP | 0402036 B1 | 12/1990 |
| EP | 0402176 B1 | 12/1990 |
| EP | 0458877 B1 | 4/1991 |

(56) References Cited

FOREIGN PATENT DOCUMENTS

| | | |
|---|---|---|
| EP | 0515324 A1 | 11/1992 |
| EP | 0547135 B1 | 6/1993 |
| EP | 0 592 410 B1 | 10/1995 |
| EP | 0 592 410 B1 | 11/1995 |
| EP | 0729364 B1 | 9/1996 |
| EP | 0756498 B1 | 5/1997 |
| EP | 0778775 B1 | 6/1997 |
| EP | 0928615 A1 | 7/1999 |
| EP | 0986348 B1 | 3/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 253 875 B1 | 4/2005 |
| EP | 1 251 803 B1 | 6/2005 |
| EP | 1469797 B1 | 11/2005 |
| EP | 1 690 515 A1 | 8/2006 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| EP | 3 181 096 A1 | 6/2017 |
| FR | 2828263 A1 | 2/2003 |
| GB | 2433700 A | 7/2007 |
| GB | 2440809 A | 2/2008 |
| JP | 2004-504111 A | 2/2002 |
| JP | 2003-515386 A | 5/2003 |
| JP | 2003-523262 | 8/2003 |
| JP | 2003-524504 | 8/2003 |
| JP | 2005-118585 | 5/2005 |
| JP | 2007-521125 A | 8/2007 |
| JP | 2007-296375 | 11/2007 |
| JP | 2008-539305 | 11/2008 |
| JP | 2009-131397 A | 6/2009 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO 98/43556 | 10/1998 |
| WO | WO-98/46165 | 10/1998 |
| WO | WO-99/37337 | 7/1999 |
| WO | WO-99/66863 | 12/1999 |
| WO | WO 00/15148 | 3/2000 |
| WO | WO-00/18445 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 2001/35870 A1 | 5/2001 |
| WO | WO 01/39700 A1 | 6/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 2002/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO-03/079928 A2 | 10/2003 |
| WO | WO 03/092554 A1 | 11/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/011534 A1 | 2/2005 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 | 7/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO-2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO-2008/035337 A1 | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/101083 A2 | 8/2008 |
| WO | WO 2008/125153 A1 | 10/2008 |
| WO | WO 2008/138584 A1 | 11/2008 |
| WO | WO-2008/150529 A1 | 12/2008 |
| WO | WO 2009/045338 A1 | 4/2009 |
| WO | WO 2009/053497 A1 | 4/2009 |
| WO | WO 2009/106545 A1 | 9/2009 |

OTHER PUBLICATIONS

English translation of Aortenklappenbioprothese erfolgreich in der Entwicklung (2 pages).
Screen shots from http://www.fraunhofer.de/presse/filme/2006/index.jsp, 2006 (2 pages).
Liang, Ma, et al., "Double-crowned valved stents for off-pump mitral valve replacement," Eur. J. Cardio-Thoracic Surgery, vol. 28, pp. 194-198 (2005) (5 pages).
Huber, Christoph H., et al. "Direct Access Valve Replacement (DAVR)—are we entering a new era in cardiac surgery?" Eur. J. Cardio-Thoracic Surgery, vol. 29, pp. 380-385 (2006) (6 pages).
English translation of DE 19546692 A1 (3 pages).
English translation of EP 1469797 B1 (15 pages).

(56) References Cited

OTHER PUBLICATIONS

File history for German Patent DE 195 46 692 filed Dec. 14, 1995 and patented Jul. 11, 2002 (111 pages).
English abstract for DE 19857887 A1 (1 page).
English abstract for DE 10335948 B3 (1 page).
Klein, Allan L. et al., "Age-related Prevalence of Valvular Regurgitation in Normal Subjects: A Comprehensive Color Flow Examination of 118 Volunteers," *J. Am. Soc. Echocardiography,* vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," *Thorac. Cardiov. Surg.,* vol. 56, pp. 328-336 (2008) (9 pages).
Gummert, J.F. et al., "Cardiac Surgery in Germany During 2006: A Report on Behalf of the German Society for Thoracic and Cardiovascular Surgery," *Thorac. Cardiov. Surg.,* vol. 55, pp. 343-350 (2007) (8 pages).

STENT FOR THE POSITIONING AND ANCHORING OF A VALVULAR PROSTHESIS IN AN IMPLANTATION SITE IN THE HEART OF A PATIENT

This application is a continuation of U.S. application Ser. No. 14/709,909, filed on May 12, 2015, which is a continuation of U.S. application Ser. No. 12/071,814, filed on Feb. 26, 2008, each of which is incorporated herein by reference in its entirety.

The present invention relates to a stent for the positioning and anchoring of a valvular prosthesis in an implantation site in the heart of a patient. Specifically, the present invention relates to an expandable stent for an endoprosthesis used in the treatment of a stenosis (narrowing) of a cardiac valve and/or a cardiac valve insufficiency.

The expression "narrowing (stenosis) of a cardiac valve and/or cardiac valve insufficiency" is intended to include a functional defect of one or more cardiac valves, which is either genetic or has developed. A cardiac defect of this type might affect each of the four heart valves, although the valves in the left ventricle (aortal and mitral valves) are affected much more often than the right-sided part of the heart (pulmonary and tricuspid valves). The functional defect can result in narrowing (stenosis), inability to close (insufficiency) or a combination of the two (combined vitium). This invention relates to an expandable stent for insetting a heart valve stent in a patient's body for treating such a heart valve defect.

In the current treatment of severe narrowing of a cardiac valve and/or cardiac valve insufficiency, the narrowed or diseased cardiac valve is replaced with a valvular prosthesis. Biological or mechanical valves models, which are typically surgically sewn into the cardiac valve bed through an opening in the chest after removal of the diseased cardiac valve, are used for this purpose. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible valvular prosthesis. Such a self-expandable endoprosthesis can be guided via a catheter system to the implantation site within the heart through an inguinal artery or vein. After reaching the implantation site, the stem can then be unfolded.

To this end, it is known that a stent may be comprised of, for example, a plurality of self-expanding longitudinal stent segments, the segments being articulated relative one another. In order to anchor the stent securely in position the an appropriate blood vessel close to the heart, anchoring barbs are frequently used to engage with the vascular wall.

An expandable stent for the fastening and anchoring of a valvular prosthesis is known from printed publication DE 10 010 074 A1, whereby the stent is essentially formed of wire-shaped, interconnected segments. DE 10 010 074 A1 proposes a stent for fastening and anchoring a valvular prosthesis, the stent having different arched elements which assume the function of fastening and supporting the valvular prosthesis at the site of implantation. Specifically, three identically-configured positioning arches spaced 120° from one another respectively are used. These positioning arches are connected to one another by means of solid body articulations. Addition to the positioning arches, complementary curved retaining arches serve to anchor the endoprothesis by pressing radially against the vascular wall following the unfolding of the stent.

However, there is a risk of inexact or incorrect implantation of a valvular prosthesis using the solutions described above. Expressed in another way. There is a need for exact positioning and longitudinal alignment of an implanted valvular prosthesis. In particular, it is only possible using great skill on the part of the attending surgeon or cardiologist—if at all—to position a stent sufficiently precisely, in both a lateral and longitudinal direction, to ensure that the associated valvular prosthesis is located in the correct area of the patient's diseased heart valve.

Among other things, inexact implantation of a sub-optimally positioned valvular prosthesis can lead to leakage or valvular insufficiency which results in considerable ventricular stress. For example, if a valvular prosthesis is implanted too far above the plane of the native heart valve, this can lead to closure or blocking of the coronary artery ostia (inlet orifice of coronaries) and thus to fatal coronary ischemia and myocardial infarction.

Therefore, for the optimal treatment of a narrowed cardiac valve or a cardiac valve insufficiency, it is necessary to position a stent, to which a valvular prosthesis is affixed, as precisely as possible at the site of implantation of the cardiac valve to be treated.

An endoprosthesis for treating aortic valve insufficiency is known from printed publication DE 20 2007 005 491 U1. The endoprosthesis comprises a valvular prosthesis and a stent to position and anchor the valvular prosthesis at the implantation site in the patient's heart. A stent having several (multiple, normally three, but two in case of bicuspid valve) positioning arches is employed in this endoprosthesis. In the implanted state of the stent, these positioning arches extend radially and serve to engage in the pockets of the native (diseased) cardiac valve to be treated. The valvular prosthesis affixed to the stent can then self-position into the plane of the cardiac valve. Retaining arches abut against the vascular wall of the aorta in the implanted state of the endoprosthesis, form a force-fit connection and are used to anchor the endoprosthesis.

While the positioning arches enable optimal positioning of the stent of this endoprosthesis at the site of implantation in the patient's heart, what cannot be ensured is that the valvular prosthesis attached to the proximal end of the stent is actually also positioned in the plane of the cardiac valve. In particular, substantial forces act on the valvular prosthesis during the filling phase of the heart cycle (diastole), which can lead to the valvular prosthesis displacing longitudinally relative the stent. Due to this longitudinal displacement of the implanted valvular prosthesis, which occurs in the heart and blood vessels especially because of the peristaltic motion of the heart, the implanted valvular prosthesis may no longer be able to provide a secure seal.

Moreover, there is the danger that, because of the longitudinal displacement of the valvular prosthesis relative the stent occurring with the peristaltic motion, the threads or sutures used to fasten the valvular prosthesis to the stent may chafe against the stent. It can therefore not be excluded that the fastening threads may fray over the course of time and thus lose their fastening function. This would result in at least a partial separation of the valvular prosthesis from the stent, which in turn can lead to leakages, an inappropriate positioning or even complete detachment of the valvular prosthesis.

On the basis of the problems outlined above, the present invention addresses the issue of providing a self-expandable endoprothesis fox treating a narrowed cardiac valve or a cardiac valve insufficiency which realizes optimum positioning accuracy and anchoring of a valvular prosthesis to be implanted. In addition, the treatment of the narrowed cardiac valve or cardiac valve insufficiency should be by way of a simple procedure to enable routine treatment of narrowed cardiac valve or cardiac valve insufficiency without major stress to the patient.

A further task of the present invention lies in specifying an endoprothesis for the treatment of a stenosed cardiac valve or a cardiac valve insufficiency, whereby the endoprothesis can be anchored securely at the site of implantation in the patent's heart. In addition, the present invention also addresses the issue of substantially preventing displacement of an implanted valvular prosthesis from its ideal site of implantation in spite of the forces acting on the endoprothesis during the filling phase of the heart cycle.

From one aspect, an expandable stent is proposed in accordance with the present invention, the scent comprising at least one fastening portion by means of which a valvular prosthesis is connected to the stent. In particular, the stent comprises both positioning arches and retaining arches. At least one positioning arch of the stent is connected with at least one retaining arch of the stent by a first connecting web. Additionally, the stent further comprises at least one auxiliary arch which interconnects the arms of respective retaining arches.

The at least one fastening portion extends along the longitudinal axis of the stent and comprises a plurality of fastening holes distributed in a longitudinal direction at discrete positions along the length of the at least one fastening portion. Thread or thin wire may be guided through each fastening hole to secure the valvular prosthesis to the stent. The advantage of this feature is that longitudinal displacement of the valvular prosthesis relative to the stent is substantially minimized once implanted and so the prosthesis is not unduly disturbed or weakened as a result of the heart's peristaltic motion.

Depending from and between a pair of fastening portions is a fastening arch, over which valve tissue is laid. The fastening arch is located inside the circumference of the stent. In this way, the prosthesis tissue is separated and held away from positioning and retaining arches, thereby reducing the likelihood of these arches chaffing the tissue which, in turn may result in damage and weakening of the prosthesis. The fastening arch serves to anchor the lower edge of the valvular prosthesis and to tension the material so the prosthesis is effective as a valve. By having a fastening portion and fastening arches, the prosthesis is fully supported and anchored within the boundary of the stent. The combination of the two fastening mechanisms also provides a failsafe should one fastening mechanism fail. This is of particular relevance with suturing since a poorly sutured prosthesis will not be as effective as it should due to additional stresses and strains imparted to the prosthesis by the sutures. Thus, the arches allow fastening of the prosthesis in a manner that does not rely solely on suturing.

In an implanted configuration, the at least one positioning arches of the stem extends from the circumference of the stent in a generally radial direction. These positioning arches are designed to engage in the pockets of the native (diseased) cardiac valve that is being replaced which, in turn allows accurate positioning of the stent. Furthermore, on implantation, a positioning arch sits between the vascular wall and a leaflet of the native heart valve. The positioning arch then co-operates with a corresponding retaining arch resulting in clipping of the native leaflet between the two arches. In this way, the positioning and retaining arches together hold the stent in position and substantially eliminate axial rotation of the stent.

The at least one retaining arch is connected to a positioning arch by a connecting web. The retaining arch extends radially in the implanted state of the stent such that the at least one retaining arch presses against the wall of the blood vessel in which the stent is deployed with a radially-acting tensioning force. In addition to the at least one retaining arch, the invention provides for the stent to further comprise at least one auxiliary arch which interconnects the respective arms of the at least one retaining arch connected to the at least one positioning arch. As with the at least one retaining arch, the at least one auxiliary arch also protrudes radially in the expanded state of the stent when implanted such that the at least one auxiliary arch also presses against the wall of the blood vessel in which the stent is deployed with a radially-acting tensioning force.

In the at least one fastening portion of the stent, by means of which the valvular prosthesis can be fastened to the stent, a plurality of fastening holes is provided. These fastening holes are longitudinally distributed at given positions on the fastening portion and guide at least one thread or thin wire to fasten the valvular prosthesis to the stent, thereby enabling a precise positioning of the valvular prosthesis on the stent. Each individual fastening hole provided in the at least one fastening portion thereby serves to guide a thread or thin wire with which the valvular prosthesis is affixed or sewn to the fastening portion of the stent.

The means provided for fastening the valvular prosthesis to the fastening portion of the scent (thread or thin wire) is guided by way of the fastening holes so that a longitudinal displacement of the valvular prosthesis relative the stent is substantially minimized. This also allows exact positioning of the valvular prosthesis relative the stent.

The secure and defined fixing of the valvular prosthesis to the at least one fastening portion of the stent moreover effectively prevents the means used to fasten the valvular prosthesis to the stent (threads or thin wires) from rubbing against the stent and thus degrading after a longer period of use.

In order to configure the plurality of fastening holes in the fastening portion, the at least one fastening portion is preferably configured as—in comparison to the respective arms of the positioning arch, retaining arch and auxiliary retaining arch—a widened segment. Thus, the fastening portion is a stent segment which comprises a relatively large amount of material, facilitating movement and position analysis when the stent is being implanted. For example, when fluoroscopy (cardiac catheterization=LHK) or ultrasound (trans-esophageal echocardiogram=TEE) is used to monitor the insertion procedure, the fastening portion of the stent is particularly distinguishable.

In manufacturing the stent used in the endoprothesis according to the invention, it is conceivable lot the stent to exhibit a structure integrally cut from a portion of tube, in particular from a small metal tube, which incorporates the positioning arches, retaining arches and auxiliary retaining arches as well as the at least one fastening portion with the defined fastening holes. Specifically, it is conceivable to use a laser to cut the stent structure from the small metal tube, whereby the structure is thereafter subject to an applicable shaping and thermal treatment process so that the stent can transform from a collapsed state during implantation into an expanded state at the site of implantation. This shaping and thermal treatment process is advantageously performed gradually in order to prevent damage to the stent structure.

Particularly preferred is for the stent to exhibit a structure integrally cut from a small metal tube in which each positioning arch is allocated one retaining arch, and in which each upper end portion of the positioning arch towards the upper end of the stent is connected with the upper end portion of the associated retaining arch via a first connecting web. The at least one fastening portion, in which the plurality of fastening holes is provided, is thereby preferably configured within an arm of the retaining arch.

It is to be understood that the term "upper" refers to the stent when viewed in its implanted state. In other words, the term "upper" refers to the distal end of the stent which, when implanted, is sited away from the heart. Similarly, use of the term "lower" refers to a proximal position on the stent which is located towards the heart when the stent is viewed in its implanted position.

A preferred realization of the stent according to invention provides for a fastening portion to be configured within each arm of the stent's retaining arch.

In order to be able to reinforce the respective retaining arches of the stent, the auxiliary arch as already mentioned above is provided and which extends from the lower ends of the fastening portion and connects the respective arms of two neighboring retaining arches.

The stent preferably exhibits an integrally-formed structure which can transform from a first predefinable shape into a second predefinable shape, whereby the stent exhibits a first predefinable shape (collapsed shape) during insertion into the patient's body and a second predefinable shape (expanded shape) once implanted. Because of the stent's design, during the transition of the stent from the first predefinable shape into the second predefinable shape, the positioning arches, retaining arches and auxiliary arches are radially expanded as a function of the cross-sectional expansion of the stent. The stent's second shape is thereby preferably selected such that when expanding, the retaining arch and the auxiliary arch abut against the wall of the blood vessel in which the stent is deployed.

To achieve a secure anchoring of the stent at the site of implantation, both the retaining and auxiliary arches should press against the wall of the vessel with a radial force, whereby this radial force can be set by subjecting the stent structure to a suitable shaping and thermal treatment process.

A preferred embodiment of the stent according to the invention provides for the positioning arches and the associated retaining arches as well as auxiliary arches each to exhibit an essentially U-shaped, T-shaped or V-shaped structure which is closed toward the lower end of the stent. It is particularly preferred for each positioning arch to be cut from the material portion of a small metal tube from which the essentially U-shaped, T-shaped or V-shaped structure of the associated retaining arch was taken. The respective auxiliary arches are preferably cut from a material portion of the small metal tube situated between the essentially U-shaped, T-shaped or V-shaped retaining arch structures.

This preferred embodiment of the stent structure thus provides for the respective retaining and auxiliary arches of the stent to form the lower region of the endoprothesis, whereby the positioning arches are configured symmetrically to the retaining arches although preferably disposed somewhat farther toward the upper region of the endoprothesis.

The respective upper ends of the positioning arches are connected to the respective upper ends of the associated retaining arches by means of a first connecting web in the upper region of the endoprothesis. The fastening portions are configured in the respective arms of the retaining arch. In the expanded state of the stent, both the lower region with the fastening portions, as well as the connecting web disposed at the upper end of the stent between the respective positioning and retaining arches, spread out so that a radially-acting force is exerted on the blood vessel wall from both the lower region of the stent as well as the upper end of the stent, thereby enabling secure anchoring of the stent at the site of implantation.

In a preferred embodiment, the stent exhibits in its first shape (collapsed shape) an outer diameter of approximately 4 to 8 mm and a length of between 30 mm and 40 mm, preferably between 34.0 and 39.0 mm, and more preferably between 34.37 mm and 38.37 mm. This allows the stent to be inserted easily into the patient's body, for example with a 21F delivery system, and to be used with a valvular prosthesis having a diameter of between 19 mm and 28 mm. The afore-mentioned length specifications are the dimensions currently preferred, based on which the stent becomes suitable for the majority of patients to be treated.

In order to achieve a particularly secure anchoring of the implanted stent with the stretched valvular prosthesis affixed thereto, it is further conceivable for the stent to be subject to a shaping and thermal treatment process during its manufacture such that the finished stent exhibits a slightly concave configuration tapering toward its lower end in its second shape.

In other words, the lower end portion of the stent; i.e., that area in which the valvular prosthesis is fastened, exhibits a somewhat tapered diameter in comparison to the upper end portion. Specifically, it has been seen that, when the stent is in it second shape and the upper end of the stent exhibits a diameter approximately 10-25% larger than the diameter of its lower end, radial forces are generated particularly at the stent's upper end. This enables a secure hold of the stent in the blood vessel without damaging the arterial wall. This configuration also provides secure anchoring that is able to withstand the peristaltic motion of the heart and the arterial wall. The somewhat lesser radial force exerted by the lower end of the stent not only serves to anchor the stent in the blood vessel but also to stretch the valvular prosthesis attached at the lower end and reliably seal the prosthesis against the arterial wall. It is of course also conceivable to design the concave configuration of the stent in its second shape to be of greater or lesser concavity.

It is preferable for the lower end area of the stent, when in its second shape, to exhibit a diameter of between 22 mm and 33 mm, preferably between 25 mm and 31 mm. It is conceivable for the stent to exhibit two or more differently dimensioned sizes whereby the optimal stent size can be selected depending upon specific patient. In addition, exact and patient-specific dimensions of the stent—starting from a given stent size—can be realized by appropriately curing the stent, in particular by a thermal treatment process.

In a particularly preferred realization, the stent comprises a valvular prosthesis, preferably a biological valvular prosthesis, which is attached to the at least one fastening portion of the stent by means of a thread or the like.

A shape memory material is preferably used as the material for the stent, the material being designed such that the stent can transform from a temporary shape into a permanent shape under the influence of an external stimulus. The temporary shape is thereby the stent's first shape (i.e. the collapsed state of the stent), while the permanent shape is assumed in the stent's second shape (i.e. in the expanded state of the stent). In particular, use of a shape memory material such as nitinol, i.e. an equiatomic alloy of nickel and titanium, allows for a particularly gentle implantation procedure when implanting the stent.

When manufacturing the stent preferably made from a shape memory material, the stent structure is preferably shaped after it has been cut from a tube. Once the desired shape has been formed, this shape is "fixed", this process being known as "programming." Programming may be effected by heating the stent structure, forming the stent into the desired shape and then cooling the stent. Programming may also be effected by forming and shaping the stent structure at lower temperature, this being known as "cold stretching." The permanent shape is thus saved, enabling the stent to be stored and implanted in a temporary, non-formed shape. If an external stimulus then acts on the stent structure, the shape memory effect is activated and the saved, permanent shape restored.

A particularly preferred embodiment provides for the external stimulus to be a definable switching temperature. It is thus conceivable that the stent material needs to be heated to a higher temperature than the switching temperature in order to activate the shape memory effect and thus regenerate the saved permanent shape of the stent. A specific switching temperature can be preset by the relevant selection of the chemical composition of the shape memory material.

It is particularly preferred to set the switching temperature to be in the range between room temperature and the patient's body temperature. Doing so is of advantage, especially with regard to the medical device being used as an implant in a patient's body. Accordingly, all that needs to be ensured in this regard when implanting the stent is that the stent is warmed up to the patient's body temperature (36° C.) at the site of implantation to activate the shape memory effect of the stent material.

The following will make reference to the included drawings in describing preferred embodiments of the stent according to the present invention in greater detail.

Figure 1B:
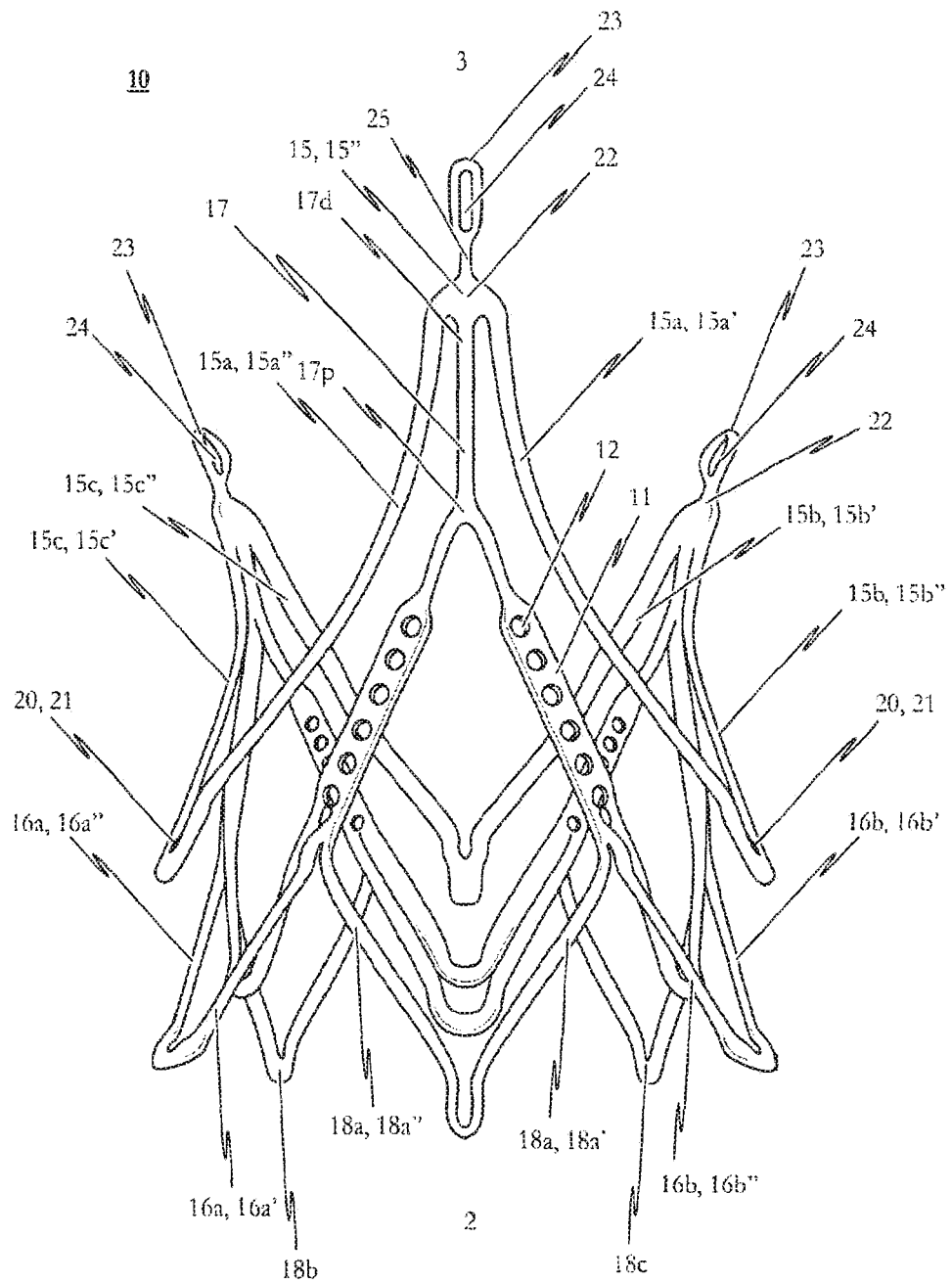
Figure 1C:
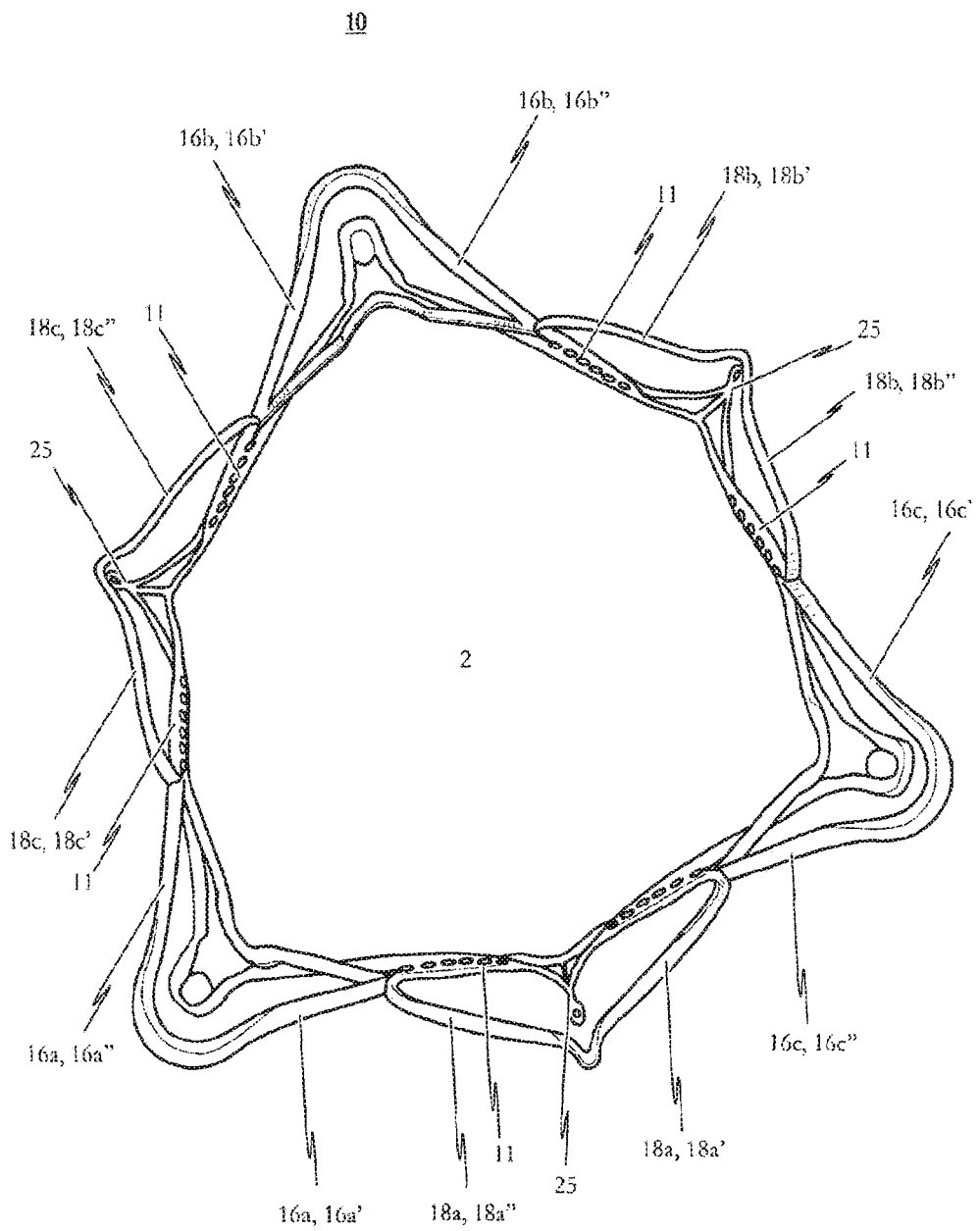
Figure 1D:
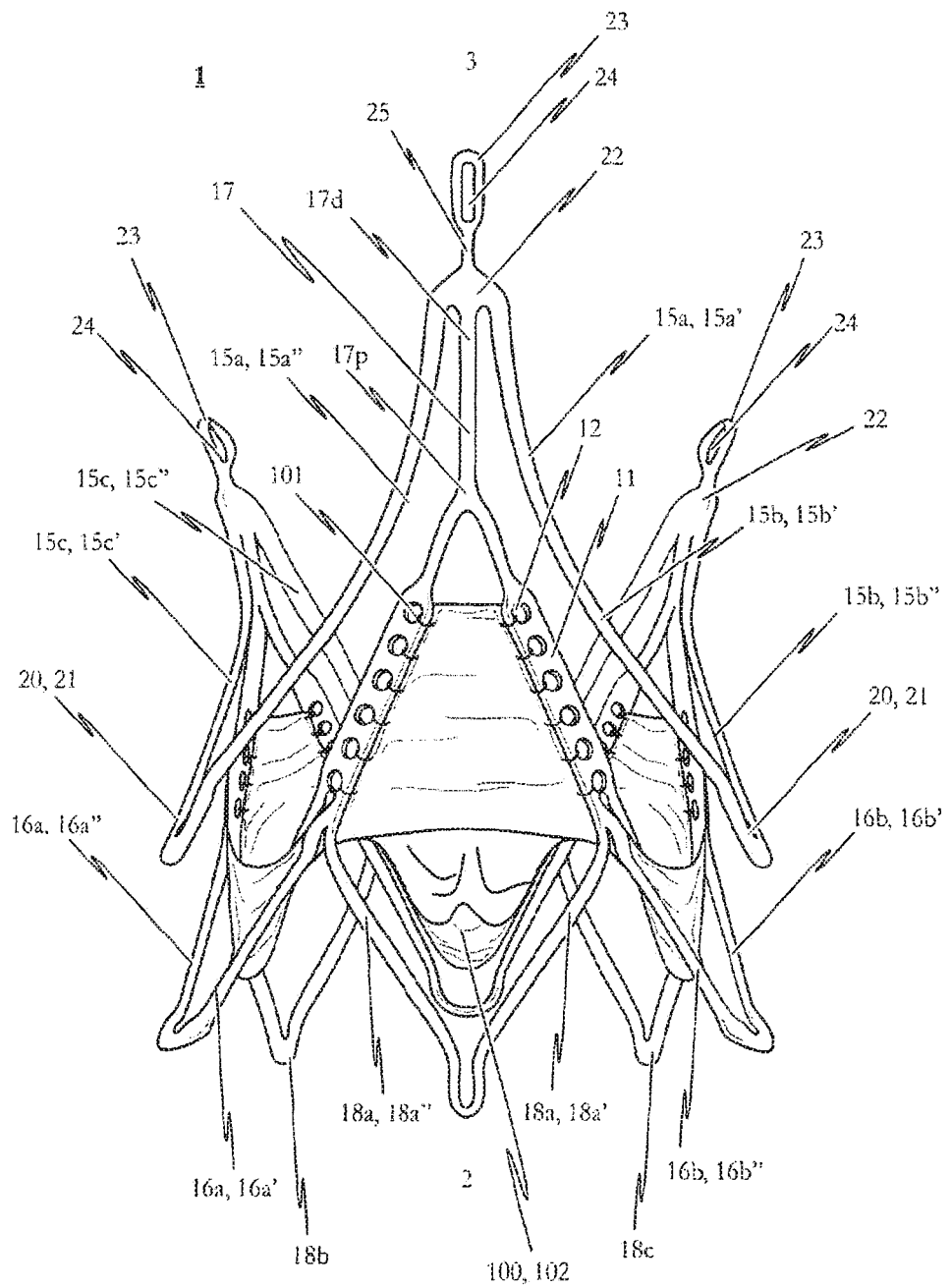
Figure 1E:
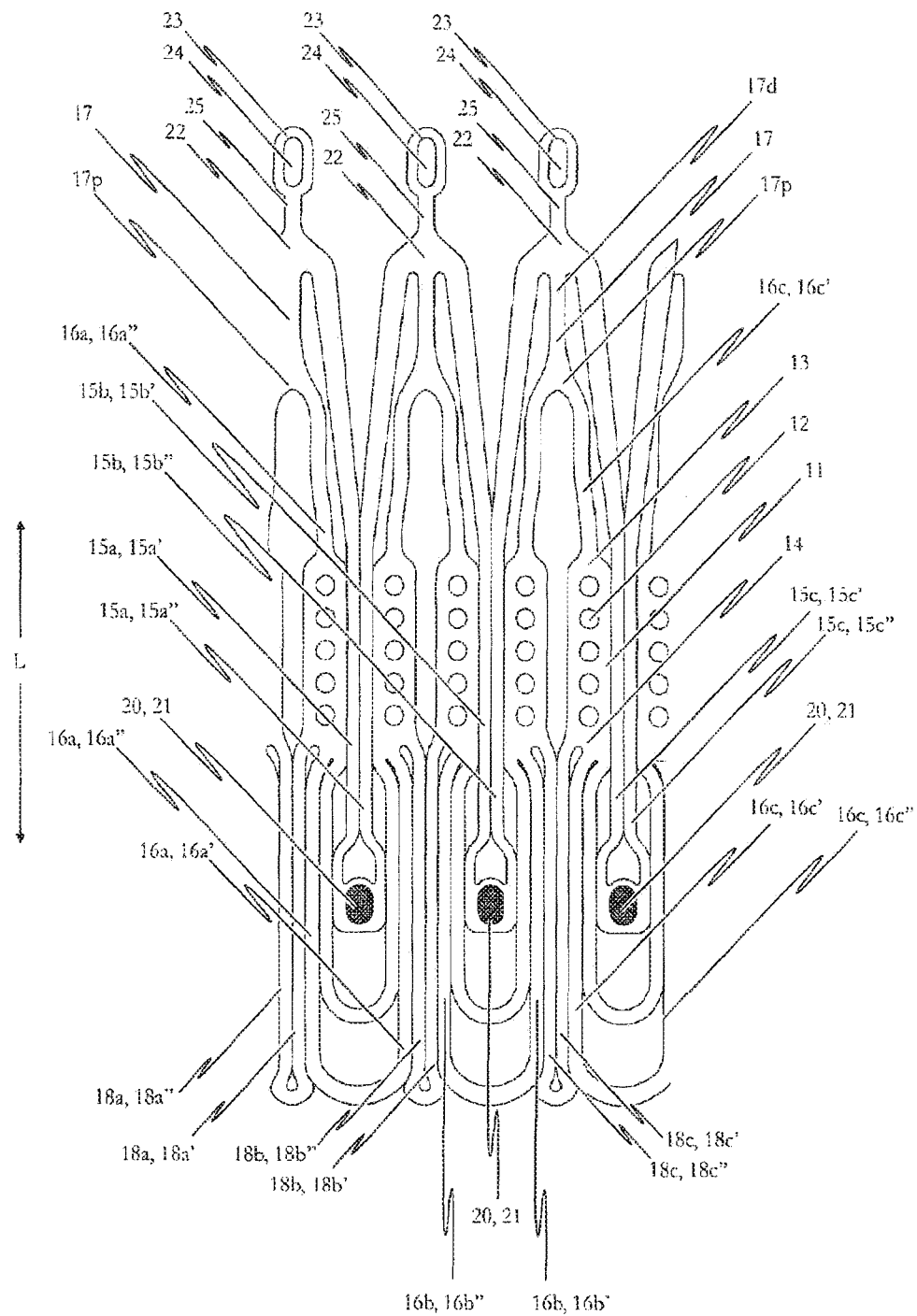
Figure 2A:
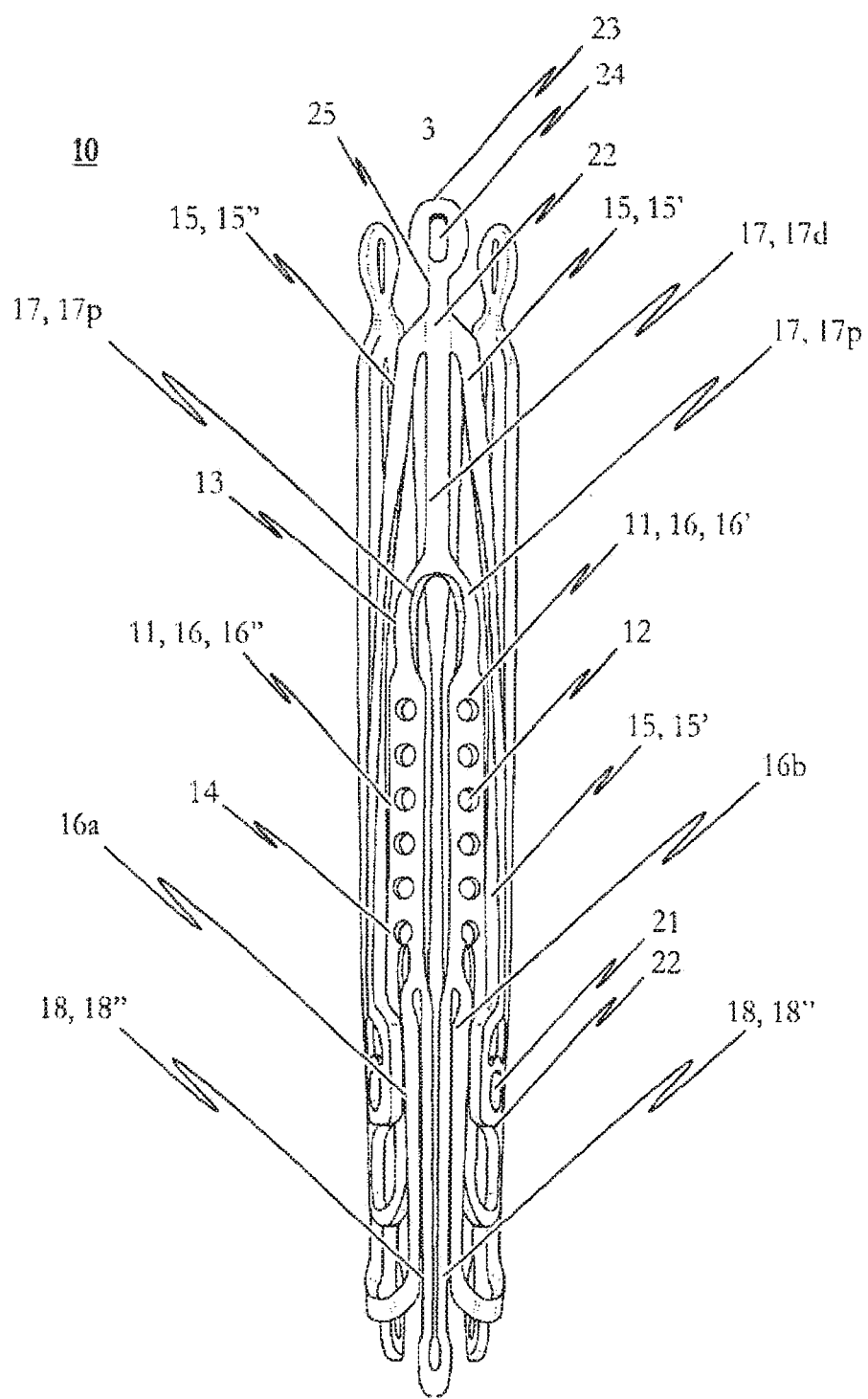
Figure 2B:
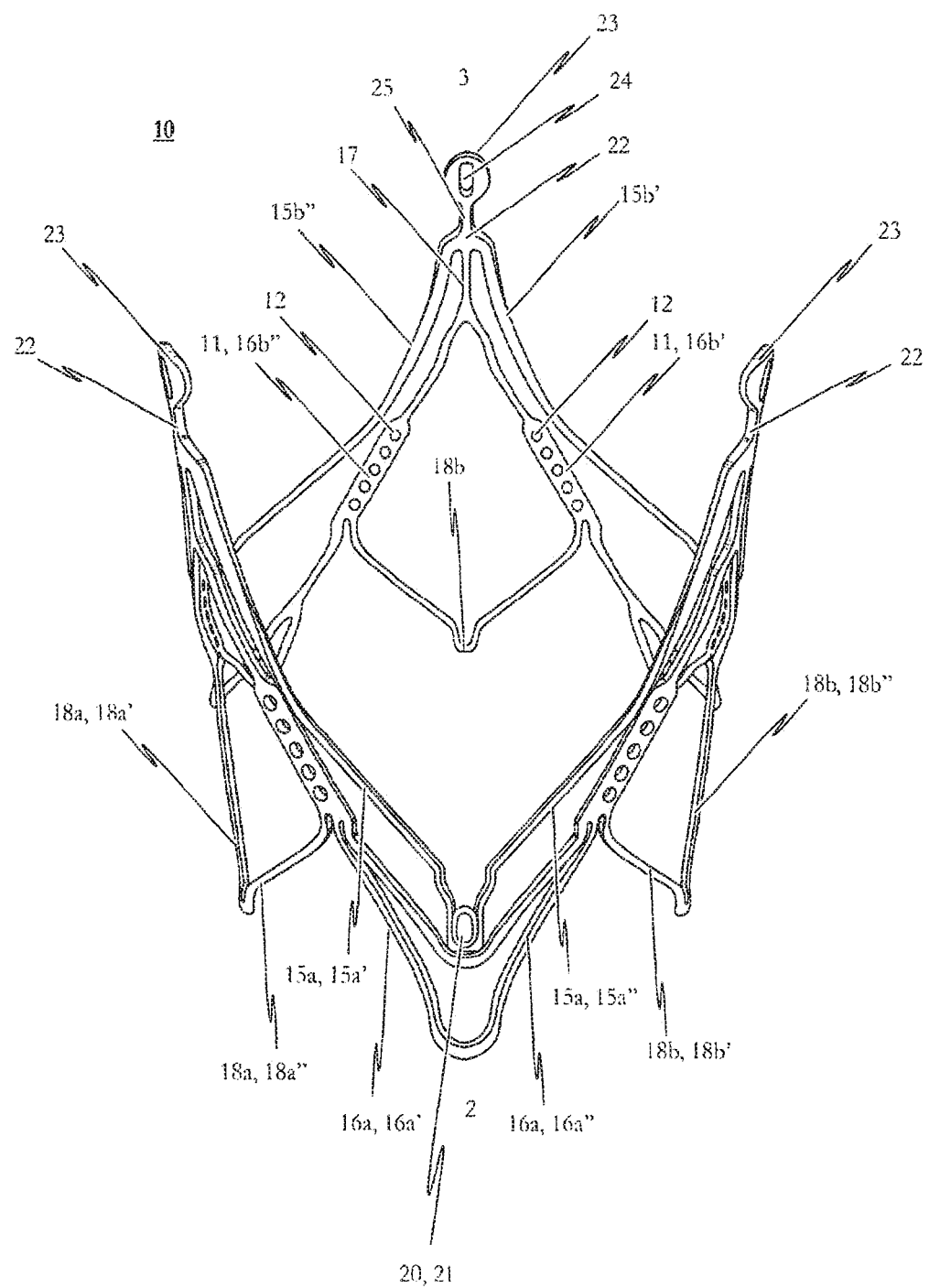
Figure 2C:
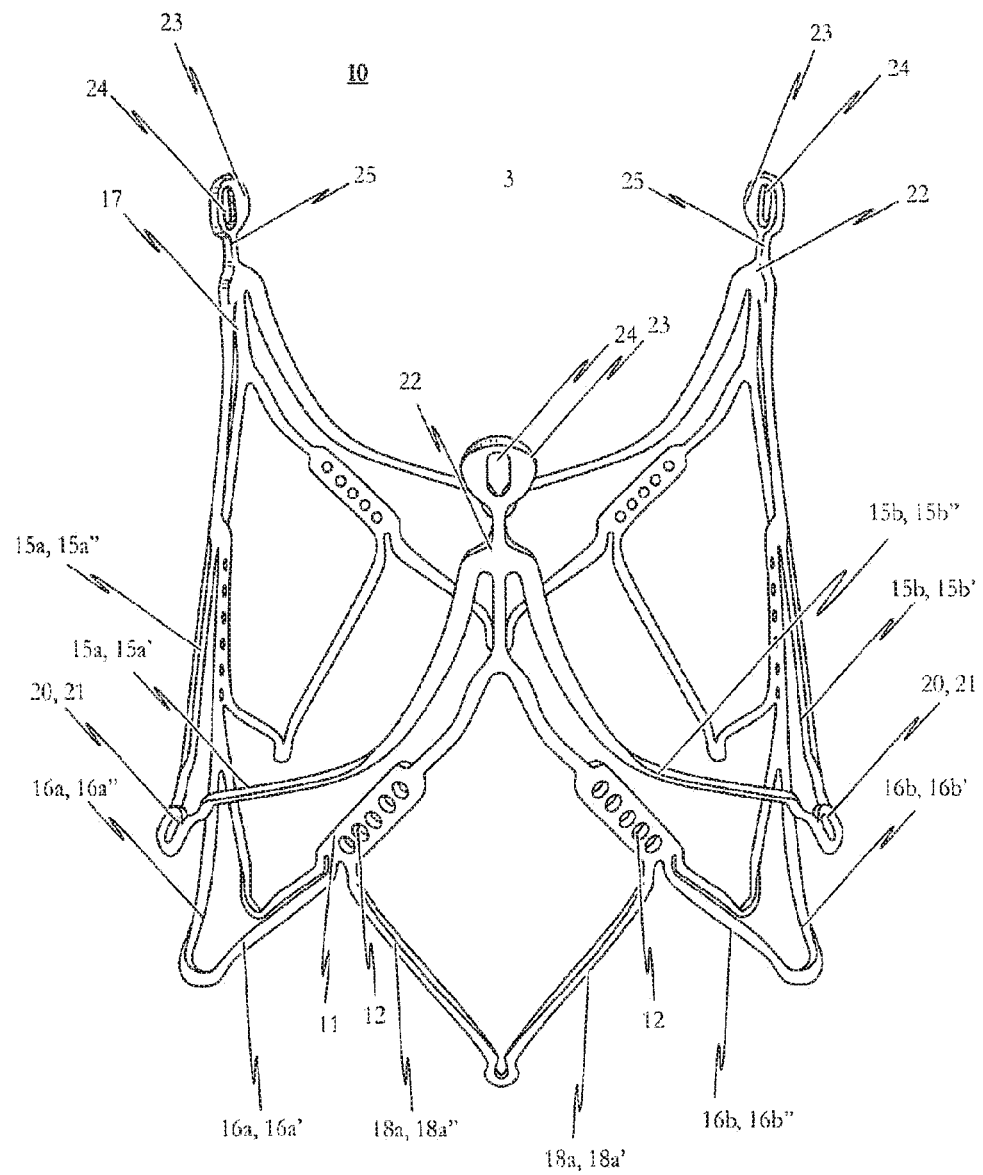
Figure 2D:
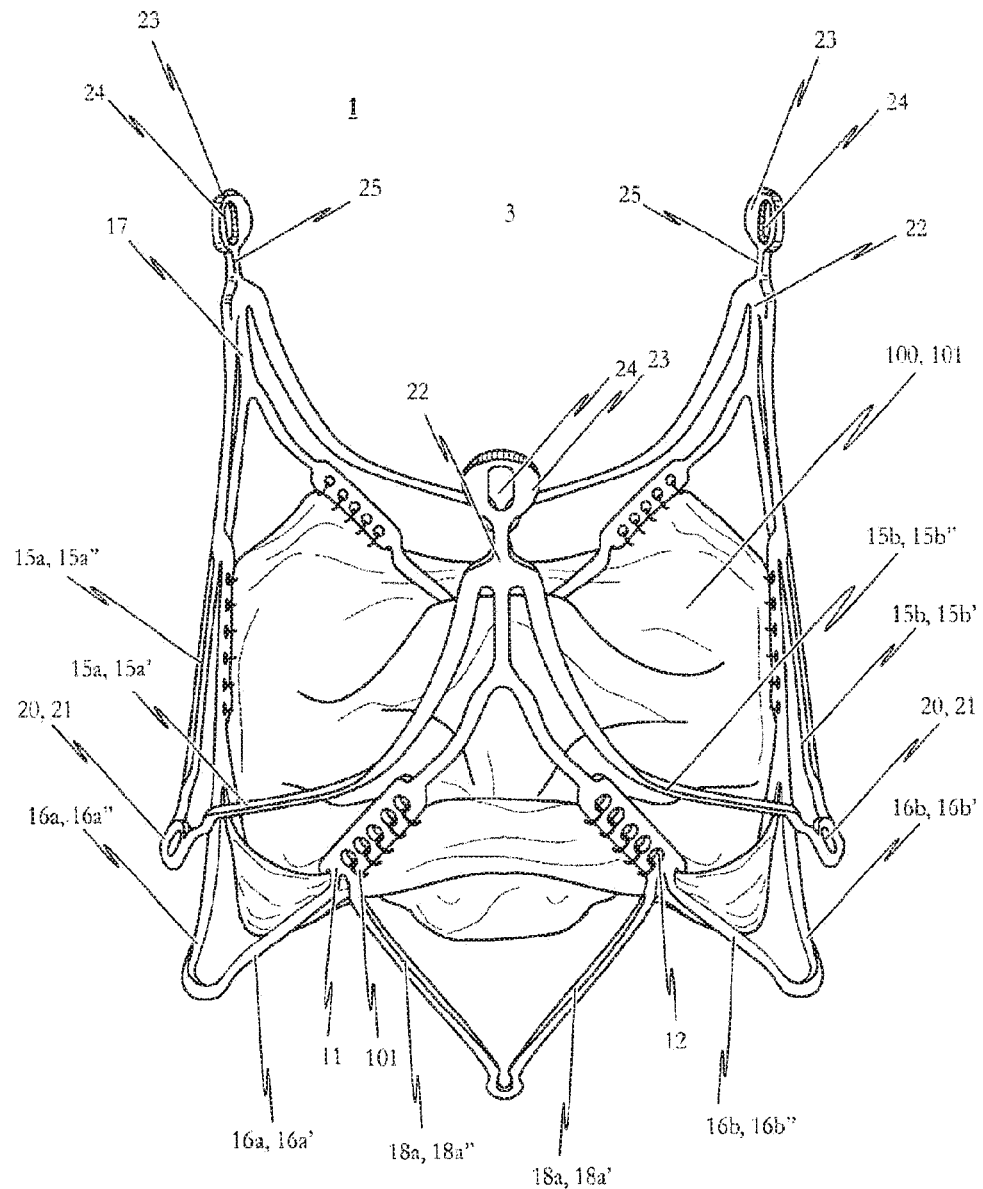
Figure 2E:
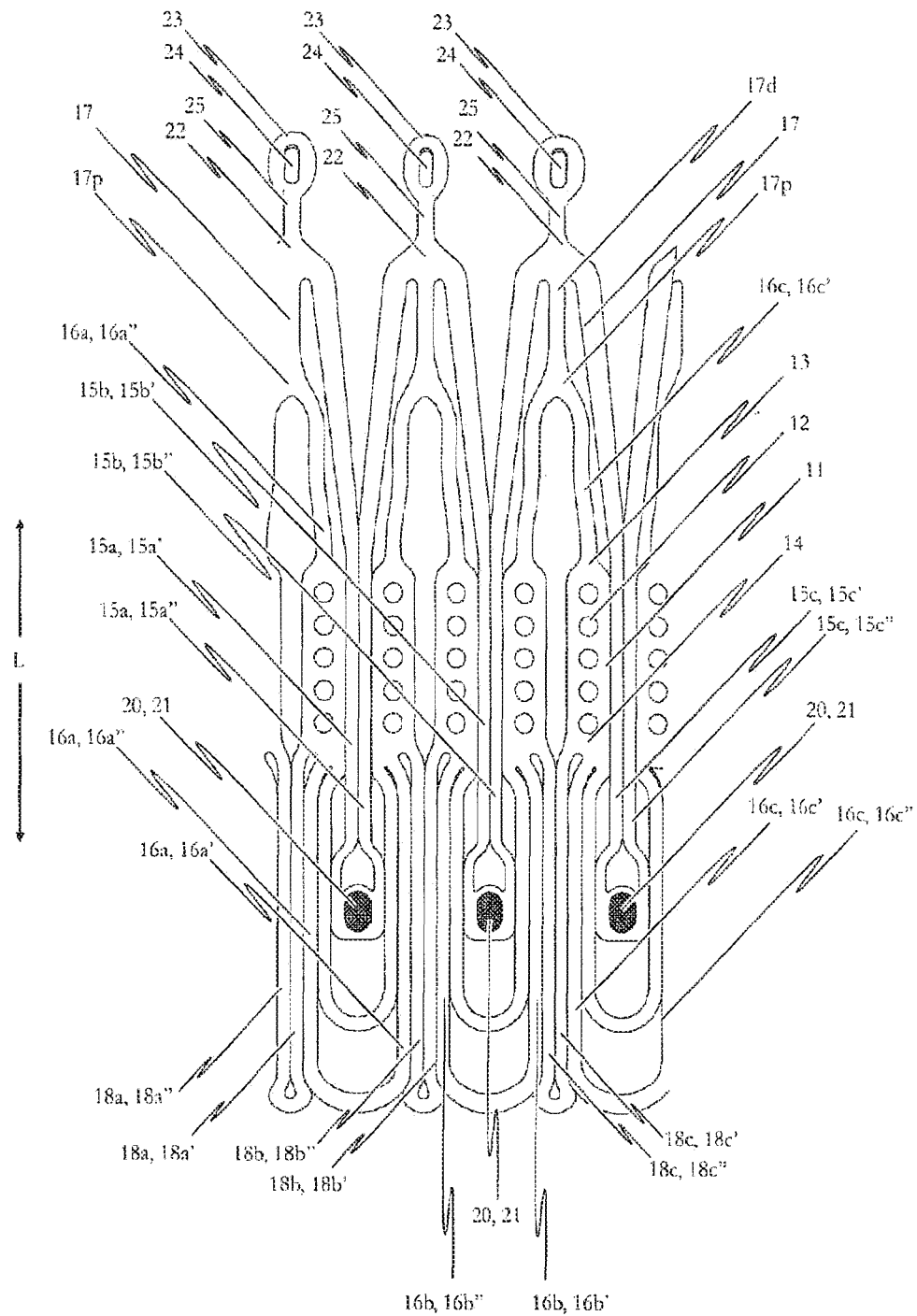
Figure 3C:
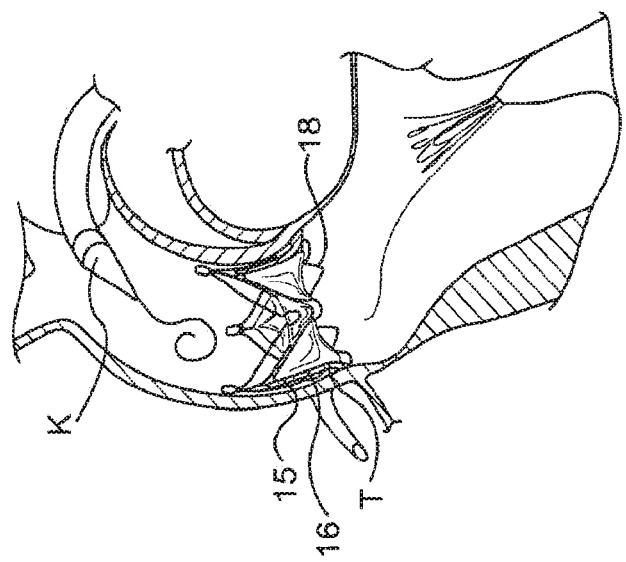
Figure 3B:
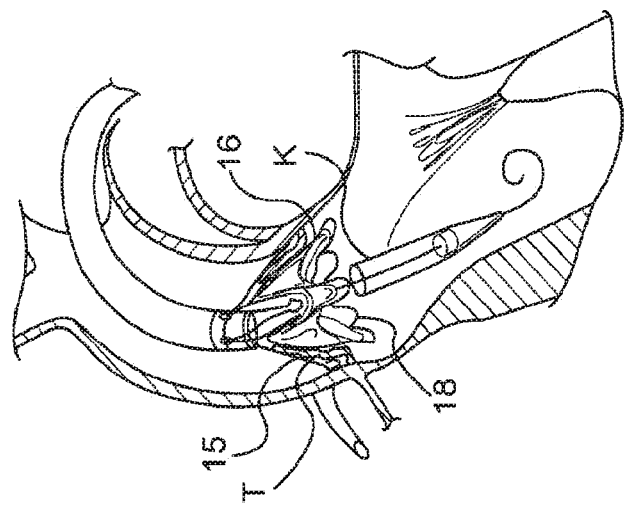
Figure 3A:
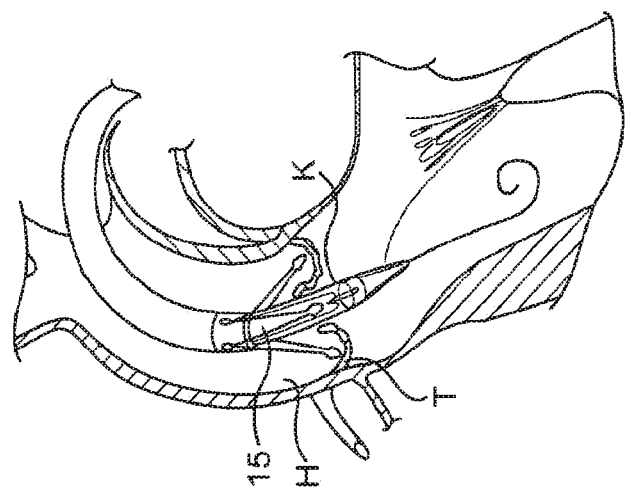

Shown are:

FIG. 1a a perspective side view of a cardiac valve stent in accordance with a first embodiment of the invention, where the cardiac valve stent is shown in its collapsed state;

FIG. 1b a perspective side view of the cardiac valve stent in accordance with the first embodiment of the invention, where the cardiac valve stent is shown in its expanded state;

FIG. 1c a perspective top plan view of the proximal end of the cardiac valve stent in accordance with the first embodiment of the invention, where the cardiac valve stent is shown in its expanded state;

FIG. 1d a perspective side view of an endoprothesis for treating a narrowed cardiac valve or a cardiac valve insufficiency, where the endoprothesis comprises the cardiac valve stent according to the first embodiment of the invention for holding a valvular prosthesis;

FIG. 1e a two-dimensional projection of a cutting pattern applicable to manufacturing the cardiac valve stent: according to the first embodiment of the invention in order to cut a cardiac valve stent pursuant FIG. 1a integrally from a portion of tube, in particular a small metal tube;

FIG. 2a a perspective side view of a cardiac valve stent according to a second embodiment of the invention, where the cardiac valve stent is shown in its collapsed state;

FIG. 2b a first perspective side view of the cardiac valve stent according to the second embodiment of the invention, whereby the cardiac valve stent is shown in its expanded state;

FIG. 2c a second perspective side view of the cardiac valve stent according to the second embodiment of the invention, where the cardiac valve stent is shown in its expanded state;

FIG. 2d a perspective side view of an endoprothesis for treating a narrowed cardiac valve or a cardiac valve insufficiency, where the endoprothesis comprises the cardiac valve stent according to the second embodiment of the invention for holding a valvular prosthesis;

FIG. 2e a two-dimensional projection of a cutting pattern applicable to manufacturing the cardiac valve stent according to the second embodiment of the invention in order to cut a cardiac valve stent pursuant FIG. 2a integrally from a portion of tube, in particular a small metal tube; and FIG. 3a-c a process sequence illustrating a transarterial implantation of an endoprothesis comprising a cardiac valve stent in accordance with the invention.

Both the right and left halves of the human heart consist of a ventricle and an atrium. These cavities are separated by the septum of the heart, divided into the atrial septum (septum interatriale) and the ventricular septum (septum interventriculare).

Blood can only flow in one direction through the chambers of the heart due to the cardiac valves situated between the atria and ventricles and in the arteries connected to the ventricles which function like mechanical valves. The superior and inferior vena cava (vena cava superior et inferior) flow into the right atrium. They supply the oxygen-depleted (venous) blood from the systemic circulation to the heart. The tricuspid valve which, like a mechanical valve, prevents a reverse flow of blood into the atrium upon ventricular contraction (systole) is situated between the right atrium and the right ventricle. It comprises three segments which are affixed like flaps to the ventricular musculature by ligaments (hence also called the "flap valve"). The two pulmonary arteries depart the right ventricle of the heart via a common trunk (truncus pulmonalis). There is also a valve between the ventricle and the pulmonary trunk, the so-called pulmonary valve. This type of valve is also called a semilunar valve due to its shape. The pulmonary arteries supply the oxygen-depleted blood to the pulmonary circulation.

Oxygen-rich (arterial) blood then usually flows through four pulmonary veins from the pulmonary circulation to the left atrium. From there, it reaches the left ventricle through a further flap valve, the mitral valve. The outflow is carried by the aorta which, like the pulmonary artery, has a semilunar valve (aortic valve).

During a heart cycle, the atria fill first while the ventricles concurrently disgorge the blood into the arteries. When the ventricular musculature relaxes, the flap valves open due to the drop in pressure in the ventricle and the blood flows in from the atria (auricular systole). This is supported by a contraction of the atria. Ventricular contraction follows: the ventricular musculature contracts, the pressure rises, the flap valves close and the blood can now only flow into the arteries through the now-opened semilunar valves. A reverse blood flow from the arteries during the relaxation phase (diastole) is prevented by the closing of the semilunar valves such that the direction of flow is determined solely by the valves.

The four cardiac valves work like mechanical valves in the heart and prevent a reverse flow of blood in the wrong direction. Each half of the heart has a flap valve (atrioventricular valve) and a semilunar valve. The atrioventricular valves are situated between the atrium and the ventricle and are called the bicuspid/mitral valve and the tricuspid valve. The semilunar valves are situated between the ventricle and the vascular outflow and are called the pulmonary valve and the aortic valve respectively.

A valve defect; i.e. a dysfunctioning of a cardiac valve's function, can affect any of the four cardiac valves, although the valves on the left side of the heart (aortic and mitral valves) are affected considerably more frequently than those on the right side of the heart (pulmonary and tricuspid valves). Dysfunction can encompass constriction (stenosis), insufficiency or a combination of the two (combined vitium).

In medicine, the term "aortic valve insufficiency", or "aortic insufficiency" for short, refers to the defective closing of the heart's aortic valve and the diastolic reverse flow of blood from the aorta into the left ventricle as a result. Depending on the severity of the aortic insufficiency and the extent of resistance to aortic depletion, the volume of reverse flow can be up to two thirds of the left ventricle's ejection volume (normal cardiac output 40 to 70 ml). This results in characteristically high blood pressure amplitude. This regurgitant bloodflow increases the diastolic filling of the left chamber and leads to a volume overload of this section of the heart, a consequence of which is eccentric hypertrophy.

Aortic valve stenosis is a valvular heart disease caused by the incomplete opening of the aortic valve. When the aortic valve becomes stenotic, it causes a pressure gradient between the left ventricle and the aorta. The more constricted the valve, the higher the gradient between the left ventricle and the aorta. For instance, with a mild aortic valve stenosis, the gradient may be 20 mmHg. This means that, at peak systole, while the left ventricle may generate a pressure of 140 mmHg, the pressure that is transmitted to the aorta will only be 120 mmHg.

In individuals with Aortic valve stenosis, the left ventricle has to generate an increased pressure in order to overcome the increased afterload caused by the stenotic aortic valve and eject blood out of the left ventricle. The more severe the aortic stenosis, the higher the gradient is between the left ventricular systolic pressures and the aortic systolic pressures. Due to the increased pressures generated by the left ventricle, the myocardium (muscle) of the left ventricle undergoes hypertrophy (increase in muscle mass).

Angina in the setting of aortic valve stenosis is secondary to the left ventricular hypertrophy that is caused by the constant production of increased pressure required to overcome the pressure gradient caused by the aortic valve stenosis. While the myocardium (i.e. heart muscle) of the left ventricle gets thicker, the arteries that supply the muscle do not get significantly longer or bigger, so the muscle may become ischemic (i.e. doesn't receive an adequate blood supply). The ischemia may first be evident during exercise, when the heart muscle requires increased blood supply to compensate for the increased workload. The individual may complain of exertional angina. At this stage, a stress test with imaging may be suggestive of ischemia.

Mitral valve insufficiency (also called mitral insufficiency) is a frequent cardiac valve defect in human medicine and also in at least some animal species. It involves a closing defect or "leakage" of the heart's mitral valve which leads to reverse bloodflow from the left ventricle into the left atrium during the ejection phase (systole).

The mitral valve functions like a mechanical valve between the left atrium and the left ventricle of the heart. It opens during the filling phase of the ventricle (diastole) and thus enables the inflow of blood from the atrium. At the beginning of the ejection phase (systole), the sudden increase in pressure in the ventricle leads to the closing of the valve and thus to a "sealing" of the atrium. In so doing, a pressure of only about 8 mmHg prevails in the atrium, while at the same time the systolic pressure of about 120 mmHg in the ventricle forces the blood along its usual path into the main artery (aorta).

In cases of severe mitral insufficiency, however, the regurgitation opening is larger than 40 mm$^2$ and the regurgitation volume greater than 60 ml, which can lead to serious and at times life-threatening changes.

In the acute stage, with a normal size to the left ventricle and the left atrium, there is a considerable increase of the pressure in the atrium and thus also in the pulmonary veins. This can be up to 100 mmHg which, given a normal condition to the pulmonary vessels, leads to immediate pulmonary edema. The then predominantly reverse blood flow can moreover result in insufficient ejection outflow into the aorta and thus decreased blood flow to all the organs.

To treat a severe narrowed cardiac valve or cardiac valve insufficiency, it is necessary for a valvular prosthesis to perform the valve function of the narrowed, diseased or diseased cardiac valve. Essential in this respect is that the valvular prosthesis is securely positioned and anchored in the implantation site in the heart; i.e. in the plane of the (diseased) cardiac valve to be replaced, so that the valvular prosthesis is not displaced or shifted despite the, at times considerable, forces acting on it. An effective seal during systole is also important.

A cardiac valve stent 10, to which the valvular prosthesis 100 is appropriately affixed, is employed in accordance with the invention to position and anchor said valvular prosthesis. A medical device for the treating of a narrowed cardiac valve or a cardiac valve insufficiency consisting of a cardiac valve stent 10 and a valvular prosthesis 100 affixed to the stent 10 will be referred to herein simply as endoprothesis 1.

FIG. 1*d* shows a perspective side view of such an endoprothesis 1 for treating a narrowed cardiac valve or a cardiac valve insufficiency, whereby the endoprothesis 1 comprises a cardiac valve scent 10 to hold a valvular prosthesis 100 in accordance with a first embodiment of the invention. FIG. 2*d* likewise shows a perspective side view of a further endoprothesis 1 for treating a narrowed cardiac valve or a cardiac valve insufficiency, whereby here a cardiac valve stent 10 in accordance with a second embodiment of the invention is employed.

The following will make reference to the included drawings in describing the presently preferred embodiments of the present invention in detail. The cardiac valve stent 10 according to the invention (hereinafter referred to simply as "stent") exhibits an expandable structure which is able to transform from a first predefinable shape in which the stent 10 is in a collapsed state into a second predefinable shape in which the stent 10 is in an expanded state. FIG. 1*a* shows a perspective side view of the stent 10 according to the first embodiment of the invention, whereby the stent 10 is in its collapsed state. FIG. 2*a* shows the collapsed stent 10 according to the second embodiment of the invention.

In the two embodiments, the scent 10 can be introduced in minimally-invasive fashion into the body of a patient in its first shape (cf. FIG. 1*a* and FIG. 2*a*) using an insertion catheter system (not explicitly shown in the drawings). During insertion, the valvular prosthesis 100 affixed to the stent 10 is likewise in a collapsed state. For the sake of clarity, however, both FIGS. 1*a* and 2*a* dispense with a representation of the valvular prosthesis 100 affixed to the stent 10.

Upon reaching the site of implantation in the patient's heart, the stent 10 transforms, preferably incrementally, into its second (expanded) shape in which also the valvular prosthesis 100 affixed to the stent 10 unfolds and expands. The second, expanded shape is a permanent shape that has been set by programming. The completely expanded stent 10 according to the first/second embodiment of the invention with the likewise completely unfolded and expanded valvular prosthesis 100 affixed thereto is shown in FIG. 1*d* and FIG. 2*d*.

FIG. 1*b* and FIG. 1*c* show the completely expanded stent 10 according to the first embodiment of the invention without the valvular prosthesis 100 from respectively different perspectives. FIGS. 2*b* and 2*c* show the completely expanded stent 10 according to the second embodiment of the invention, likewise without the valvular prosthesis 100, from respectively different perspectives.

The following will initially make reference to FIGS. 1*a* to 1*e* in describing the first embodiment of the inventive cardiac valve stent 10.

The stent 10 according to the first embodiment exhibits a structure integrally cut from a portion of tube, in particular a small metal tube. The cutting pattern used to form the design of the stent is depicted in a two-dimensional projection in FIG. 1*e*.

In detail, the stent 10 of the depicted first embodiment comprises a total of three positioning arches 15*a*, 15*b*, 15*c* which assume the function of self-positioning the stent into the plane of the pulmonary valve (valva trunci pulmonalis) or aortic valve (valva aortae). The positioning arches 15*a*, 15*b*, 15*c* exhibit a rounded head portion 20 which engages in the pockets T of the (diseased) cardiac valve to be treated during positioning of the stent 10 at the site of implantation in the heart (cf. FIG. 3*a*).

Providing a total of three positioning arches 15*a*, 15*b*, 15*c* allows for the required positioning accuracy of stent 10 in the direction of rotation. The invention is of course not limited to the use of a total of three positioning arches.

The head portions 20 of the positioning arches 15*a*, 15*b*, 15*c*, respectively pointing towards the lower end 2 of the stent 10, are correspondingly rounded so that the vascular wall will not be damaged when the positioning arches 15*a*, 15*b*, 15*c* engage in the pockets T of the cardiac valve H to be replaced. It is moreover preferred with respect to improving movement and position analysis during the implanting of the stent 10 for reference markers 21 to be provided on or within the head portions 20 of the positioning arches 15*a*, 15*b*, 15*c*. Radio opaque markers or markers which can be activated by infrared or ultrasound lend themselves particularly well hereto.

Specifically, the positioning arches 15*a*, 15*b*, 15*c* respectively exhibit an essentially U-shaped or V-shaped structure which is closed to the lower end of stent 10. Accordingly, each positioning arch 15*a*, 15*b*, 15*c* has a total of two arms 15*a*', 15*a*", 15*b*', 15*b*", 15*c*', 15*c*" respectively extending from the head portion 20 of the associated positioning arch 15*a*, 15*b*, 15*c* toward the upper end 3 of stent 10. By doing so, each two adjoining arms of two neighboring positioning arches are connected to one another via a connecting portion 22.

For implanting and explanting the stent 10 with a suitable catheter system, the stent 10 comprises catheter retaining means 23 at its upper end 3. The respective connecting portions 22, via which two respectively adjoining arms of two neighboring positioning arches are connected together, are respectively connected to catheter retaining means 23 via a connecting web 25. The connecting webs 25, which connect the connecting portions 22 to the associated catheter retaining means 23, will herein be referred to as "second connecting web 25."

In the stent 10 according to the first embodiment of the invention, the catheter retaining means 23 comprise oval-shaped heads which each respectively comprise a likewise oval-shaped eyelet 24. Conceivable hereto would be providing a crown with a total of three protruding elements in the tip of a catheter of a catheter system used to implant/explant stent 10. The protruding elements of the crown are thereby to be configured complementary to the eyelets 24 which are disposed on the catheter retaining means 23 provided at the upper end 3 of stent 10 and configured as catheter retaining heads. This realization would enable the protruding elements of the crown to form a releasable engagement with the upper area 3 of stent 10 to releasably attach stent 10 to the tip of the catheter of the catheter system used to implant/explant stent 10.

The upper end portion 17*d* of a first connecting web 17 extending essentially in longitudinal direction L of stent 10 furthermore opens to each connecting portion 22 between the two arms 15*a*', 15*a*", 15*b*', 15*b*", 15*c*', 15*c*" of two neighboring positioning arches 15*a*, 15*b*, 15*c* in addition to the previously-mentioned second connecting web 25. As can be seen in FIG. 1*b*, the respective first connecting webs 17 are of essentially Y-shaped configuration and each exhibit a structure that is spread at its lower end 17*p* which gives way to the respective arms 16*a*', 16*a*", 16*b*', 16*b*", 16*c*', 16*c*" of two neighboring retaining arches 16*a*, 16*b*, 16*c*.

This stent design achieves an axially symmetrical structure, whereby each positioning arch 15*a*, 15*b*, 15*c* is allocated one retaining arch 16*a*, 16*b*, 16*c*. The stent 10 of the first embodiment depicted in FIGS. 1*a* to 1*d* thus comprises a total of three retaining arches 16*a*, 16*b*, 16*c* which constitutes a retaining segment of stent 10 for accommodating a valvular prosthesis 100 as depicted for example in FIG. 1*d*.

In the state of the stent 10 shown in FIG. 1*a*, in which stent 10 is in its first (collapsed) shape, the respective arms 15*a*', 15*a*", 15*b*', 15*b*", 15*c*', 15*c*" of the positioning arches 15*a*, 15*b*, 15*c* directly adjoin the respective arms 16*a*', 16*a*", 16*b*', 16*b*", 16*c*', 16*c*" of the associated retaining arches 16*a*, 16*b*, 16*c*.

Reference is made to FIG. 1*b*, in which the stent 10 pursuant the first embodiment is shown in its second shape. It can be particularly recognized from this representation that each positioning arch 15*a*, 15*b*, 15*c* and associated retaining arch 16*a*, 16*b*, 16*c* respectively exhibit an essentially U-shaped or V-shaped structure which is closed towards the lower end 2 of the stent 10. Specifically, each positioning arch 15*a*, 15*b*, 15*c* is cut from a material section of a portion of a tube from which the essentially U-shaped or V-shaped structure of the associated retaining arch 16*a*, 16*b*, 16*c* was taken, as can be seen from the cutting pattern depicted in FIG. 1*e*.

A comparison of FIG. 1*a* to FIG. 1*b* shows that, upon the stent 10 expanding; i.e. when the stent 10 transforms from its first shape into its second shape, the stent 10 shortens in the longitudinal direction L while simultaneously enlarging in cross-section. In the expanded state of stent 10, the respective positioning arches 15*a*, 15*b*, 15*c* are expanded more in the radial direction at the lower end 2 of the stent 10 compared to the upper end 3 of stent 10. Since they protrude more in the radial direction, the positioning arches 15*a*, 15*b*, 15*c* can be deployed into the cardiac valve pockets T of the cardiac valve H to be replaced in particularly easy manner.

Even when a certain anchoring of the stent 10 is achieved at the site of implantation in the heart due to the positioning arches 15a, 15b, 15c already protruding radially from stent 10 in the expanded state of the stent 10, it is noted that the contact force acting on the vascular wall from the positioning arches 15a, 15b, 15c is insufficient to securely anchor the stent 10 at the site of implantation. The previously-mentioned retaining arches 16a, 16b, 16c, which form the lower end 2 of stent 10, are provided for this reason. The retaining arches 16a, 16b, 16c protrude radially from the circumference of the stent 10 in its expanded state such that the retaining arches 16a, 16b, 16c press against the wall of the blood vessel in which the stent is deployed with a radially-acting contact force.

In addition to retaining arches 16a, 16b, 16c, the stent 10 further comprises auxiliary arches 18a, 18b, 18c, which likewise exert a radially-acting contact force against the wall of the blood vessel in the implanted state of stent 10, thereby improving anchoring of stent 10 at the site of implantation.

As can be seen from FIG. 1b, stent 10 pursuant the first embodiment comprises a total of three essentially U-shaped or V-shaped auxiliary arches 18a, 18b, 18c which are closed towards the lower end 2 of said scent 10. Each auxiliary arch 18a, 18b, 18c connects a first retaining arch 16a, 16b, 16c with a second retaining arch neighboring the first retaining arch.

In a top plan view of the lower end region 2 of the expanded stent 10 (cf. FIG. 1c), the lower end region 2 exhibits a dodecagonal polygonal structure formed from the individual arms 16a', 16a", 16b', 16b", 16c', 16c" of retaining arches 16a, 16b, 16c and the individual arms 18a', 18a", 18b', 18b", 18c', 18c" of the auxiliary arches 18a, 18b, 18c. This stent design particularly provides a total of six arches 16a, 16b, 16c, 18a, 18b, 18c uniformly distributed around the lower end region 2 of stent 10, each of which press against the vascular wall and effectively hold the stent 10 in position in the expanded and implanted state of stent 10.

To recapitulate, providing retaining arches 16a, 16b, 16c on the one hand and auxiliary arches 18a, 18b, 18c on the other results in a radial force being exerted on the vascular wall by the respective lower end portions of these arches. This ensures both a secure seal of a valvular prosthesis 100 affixed to stent 10 relative the vascular wall, as well as a secure anchoring of the stent 10, at the site of implantation in the heart.

In addition to the contact force exerted on the vascular wall by way of the retaining arches 16a, 16b, 16c and auxiliary arches 18a, 18b, 18c, it is conceivable for the upper end region 3 of stent 10 to expand radially 10-25% more—in the expanded state of stent 10—compared to the lower end region 2. This gives the stent 10 a slight concave structure which tapers towards the lower end region 2. This ensures secure anchoring of the stent 10 within the vessel by the upper end region 2 of the stent 10 pressing against the vascular wall.

Furthermore, to ensure that minimal longitudinal displacement of a valvular prosthesis affixed to stent 10 can occur relative stent 10, even during the peristaltic movement of the heart and the blood vessel in which stent 10 is deployed, the embodiment of the inventive stent 10 depicted in the drawings provides for the stent 10 to comprise a plurality of fastening portions 11a to 11f extending in the longitudinal direction L of stent 10, by means of which a valvular prosthesis 100 is affixed to the stent 10. Reference is made to FIG. 1d which shows a perspective side view of an endoprothesis 1 for treating a narrowed cardiac valve or a cardiac valve insufficiency, whereby the endoprothesis 1 comprises the stent 10 pursuant the first embodiment of the invention for holding a valvular prosthesis 100. The valvular prosthesis 100 comprises at least one valve flap 102 made from a biological or synthetic material.

It will be appreciated that the valvular prosthesis may be made from any suitable material, including biological valves removed from animals such as pigs and horses, man-made biological valves created from connective tissue such as pericardium, tissue grown from cell cultures, and man-made materials and fabrics such as nitinol.

In detail, the first connecting webs 17 of stent 10 connect with connecting portions 22 via their upper ends 17d and with the upper ends 13 of fastening portions 11 via their lower ends 17p. The respective lower ends 14 of the fastening portions which are connected to one and the same connecting web 17 are thereby connected together via an essentially U-shaped or V-shaped auxiliary arch 18a, 18b, 18c which is closed towards the lower end 2 of stent 10.

Specifically, the first embodiment of the inventive stent 10 is shown in FIG. 1d in its expanded state, whereby a valvular prosthesis 100 is fastened to said scent 10 by means of a thread 101 or a thin wire and stretched by the stent 10. It is easily recognized that the widening of the center area and the lower end region 2 of stent 10 at which the valvular prosthesis 100 is disposed achieves spreading of the valvular prosthesis. At the same time, the lower end portions of the retaining arches 16a, 16b, 16c and the auxiliary arches 18a, 18b, 18c exert a radial force on the (not shown in FIG. 1d) vascular wall.

As can be seen from FIG. 1d, a defined plurality of fastening holes 12 are configured in the respective fastening portions 11a to 11f of stent 10, the same being arranged to be distributed at predefined longitudinal positions along the fastening portions 11a to 11f. The thread 101 or thin wire with which the valvular prosthesis 100 is attached to stent 10 is guided through each respective fastening hole 12.

Both components constituting the endoprothesis 1, namely the stent 10 and the valvular prosthesis 100, are preferably not connected together until directly prior to the surgical procedure. This is of advantage in terms of transport and storage since the stent 10 is a relatively sturdy component mechanically and can be stored for a long period of time without degradation. This is particularly true when the stent 10 is stored in its second shape; i.e. in the expanded state, and not brought into its first (collapsed) shape until directly prior the surgical procedure.

It can be noted from FIGS. 1b and 1d that the respective fastening portions 11a to 11f are configured in the respective arms 16a', 16a", 16b', 16b", 16c', 16c" of retaining arches 16a, 16b, 16c of stent 10. The size of the fastening holes 12 configured in the fastening portions 11a to 11f should be adapted to the thickness of the thread 101 or wire used to fasten the valvular prosthesis 100 to the stent 10.

The cross-sectional shape to the fastening holes 12 may also be adapted to the cross-sectional shape of the thread 101 or wire used to fasten the valvular prosthesis 100. This allows fixing of the valvular prosthesis 100 to the stent 10 at a precise predefined position relative the stent 10. By providing of a plurality of fastening holes 12 to anchor the valvular prosthesis 100 to the stent 10, precise positioning of the valvular prosthesis an stent 10 is achieved.

Because the fastening holes 12 are adapted to the thickness and/or the cross-sectional shape of the thread 101 or wire used to affix the valvular prosthesis 100 to the stent 10, relative movement between the stent 10 and the valvular prosthesis 100 due to the peristaltic motion of the heart can be effectively prevented when the endoprothesis 1 is implanted. The valvular prosthesis 100 is thus fastened to the stent 10 with minimal play, based on which frictioninduced wear of the thread 101 or wire used to affix the valvular prosthesis is minimized. As shown in the figures the fastening holes 12 have a circular cross-sectional shape.

As already mentioned, the fastening holes 12 configured in the respective fastening portions 11a to 11f may be of different diameters, numbers or cross-sectional shapes (oval, square, etc) according to the diameter of a thread 101 used for affixing the valvular prosthesis 100 to the stent 10, and/or according to the sewing technique utilized for affixing the valvular prosthesis 100 to the stent 10. The diameter, number and/or cross-sectional shape of at least one of the fastening holes 12 may also serve as an indication of the type of the endoprosthesis 1, i.e. the medical device used in the treatment of a narrowing of a cardiac valve and/or a cardiac valve insufficiency. In this respect, the diameter, number and/or cross-sectional shape of the at least one fastening hole 12 may be used for identification to differentiate between different sizes or types of valvular prostheses 100 adapted to be fixed on the stent 10, or may be used for identification to differentiate between different sizes or types of endoprostheses 1, if a valvular prosthesis 100 is already fixed to the stent 10. For example, a small-sized stent 10 having a small-sized valvular prosthesis 100 fixed thereto or a small-sized stent 10 adapted and configured for carrying a small-sized valvular prosthesis 100 could have circular fastening holes 12 whilst a large-sized stent 10 having a large-sized valvular prosthesis 100 fixed thereto or a large-sized stent 10 adapted and configured for carrying a large-sized valvular prosthesis 100 may have triangular fastening holes 12. This allows the surgeon/cardio staff to easily and visually tell different valve sizes, stent types and/or types of the endoprosthesis apart without the need to measure.

The fastening portions 11a to 11f of the stent 10 (onto which the valvular prosthesis 100 is sewn or sewable) do not change their shape when the stent 10 is compressed, e.g. when the stent 10 is in its first (collapsed) shape shown in FIG. 1a. This phenomenon occurs when standard tube stents are used, Thus the risk of thread wear is minimal.

The stent 10 in accordance with the second embodiment depicted in FIGS. 2a to 2c is fundamentally identical in structural and functional regard to the stent 10 according to the first embodiment depicted in FIGS. 1a to 1c. The same also holds true for the cutting pattern depicted in FIG. 2e which is, in principle, comparable to the cutting pattern according to FIG. 1e. A detailed description of the common features will therefore not be provided.

The only difference to be seen is in the configuration of the catheter retaining means 23 provided at the distal end 3 of stent 10. In contrast to the first embodiment of the inventive stent 10, heads of an essentially round configuration are used as catheter retaining means 23 in the second embodiment, in each case provided with essentially oval eyelets 24.

As already indicated, the stent 1 according to the present invention preferably exhibits a structure integrally cut from a portion of tube, and in particular from a small metal tube, in which a retaining arch 16a, 16b, 16c is allocated to each positioning arch 5a, 15b, 15c, and with which each retaining arch 16a, 16b, 16c is connected by means of an auxiliary arch 18a, 18b, 18c, whereby a fastening portion 11 with a specific number of fastening holes 12 is configured in each arm 16a', 16a", 16b', 16b", 16c', 16c" of retaining arch 16a, 16b, 16c.

FIGS. 1e and 2e each show a two-dimensional projection of a cutting pattern which can be used in the manufacture of the stent 10 pursuant the first or second embodiment of the invention in order to integrally cut a one-piece stent 10 from a portion of tube, in particular a small metal tube. It is evident that, on the one hand, the inventive stent 10 dispenses with fixed-body joints or other similar connective devices between the individual components of stent 10 (positioning arch, retaining arch, auxiliary arch). On the other hand, a stent 10 is provided which exhibits, with minimum longitudinal extension, the functionality of positionability as provided by the positioning arches 15a, 15b, 15c on the one hand and, on the other, the functionality of the defined fastening of a valvular prosthesis 100, as provided by the fastening portions 11 configured in the respective arms 16a', 16a", 16b', 16b", 16c', 16c" of the retaining arch 16a, 16b, 16c.

In addition to its retaining arches 16a, 16b, 16c, the stent 10 further comprises auxiliary arches 18a, 18b, 18c which enable a particularly secure anchoring of stent 10 in the site of implantation in the heart.

The stent 10 is preferably made from a shape memory material. The state of stent 10 shown in FIG. 1a or FIG. 2a, in which the stent 10 is in its first shape and thus in its collapsed state, is the so-called "temporary" shape of the stent structure made from a shape memory material. When an external stimulus acts on the stent structure according to FIG. 1a or FIG. 2a, the shape memory effect is activated and thus the predefined permanent shape saved during the manufacture of the stent 10 as pursuant, for example, FIG. 1b or FIG. 2b, is restored.

Said external stimulus is preferably a specifiable switching temperature whereby, to activate the shape memory effect and thus regenerate the saved permanent shape of the stent 10, the stent material is warmed to a higher temperature than the switching temperature. By selecting a suitable chemical composition of the material used for stent 10, a specific switching temperature can be predefined. In the preferred embodiment of the inventive solution, the switching temperature ranges from between about 20° C. and the body temperature of the patient.

When implanting the stent 10, it is conceivable for the stent 10 to be cooled during the insertion procedure. Once the stent 10 has been guided to its desired site of implantation, i.e. to the native cardiac valve H (cf. FIG. 3a), preferably using a suitable insertion catheter system, the cooling can be stopped. The stent 10 is then allowed to warm up to the patient's body temperature (36° C.) and the shape memory effect of the stent material is thus activated. Due to the self-expanding property of stent 10 having been triggered, radial forces are generated which act on the individual components of the stent, in particular on the positioning arches 15a, 15b, 15c, the retaining arches 16a, 16b, 16c and the auxiliary arches 18a, 18b, 18c of the stent 10.

The inventive stent 10, as well as the insertion catheter system used to implant the stent, are preferably configured so that the stent 10 with the valvular prosthesis 100 affixed thereto can be introduced transarterially into the body of the patient. In one example, the stent 10 is accommodated in the tip of the catheter of the insertion catheter system, the catheter tip being introduced into the body via, for example, puncture of the A. femoris communis (inguinal artery).

Alternatively, the stent 10 according to the invention is also suited for transapical implantation, in which—coming from the apex of the heart—the catheter tip of the insertion catheter system is advanced to the aortic valve through, for example, the left ventricle. With a catheter tip modified accordingly, an analogous implantation of the stent 10 with the valvular prosthesis 100 is thus possible.

Regardless of whether the stent 10 is delivered to the site of implantation via a transarterial or transapical approach, the tip of the catheter of the insertion catheter system is preferably advanced to the implantation site using angiographic (angiography) and echocardiographic (ultrasound) control. The actual implantation of stent 10 with the attached valvular prosthesis 100 then follows.

FIGS. 3a to 3c schematically show the process sequence to illustrate transarterial implantation of an endoprothesis 1 comprising a stent 10 in accordance with the invention. As shown, the implantation of the stent 10 with the valvular prosthesis 100 attached thereto ensues such that the individual components of the stent 10 accommodated in the catheter tip K are successively released by appropriately manipulating the catheter tip K of an insertion catheter system.

The catheter system used to implant the inventive stent 10 is ideally configured such that a liquid cooling agent can be fed through a hollow interior of the catheter system to catheter tip K. The liquid cooling agent, for example in the form of a saline solution, maintains the stent 10 accommodated in the catheter tip K at a temperature below the switching temperature while the catheter tip K is being advanced to the site of implantation. This is of particular advantage when a shape memory material is provided as the material of the stent 10. This is because the stent 10 transforms from a temporary shape into a permanent shape upon the influence of an external stimulus. The temporary shape is the first shape of stent 10 (in collapsed state, when the stent 10 is accommodated in the catheter tip K of the insertion system) and the "permanent shape" is the second shape of stent 10 (the expanded state of the stent 10 after the stent 10 has been released from the catheter tip K).

It is to be noted that the "permanent shape" of the expanded stent 10 conforms to the native shape of its environment. This allows for variations in the shape of the environment at the site of implantation which will vary from patient to patient. This property of stent 10, related to the "permanent shape" of the expanded stent 10 automatically adapting completely to the native shape of its environment, will thus always ensure that the valvular prosthesis 100 is optimally implanted.

Because a shape memory material such as nitinol, i.e. an equiatomic alloy of nickel and titanium, can be used for the inventive stent 10, a particularly gentle implantation procedure is achievable when implanting the stent 10 with the valvular prosthesis 100 affixed thereto.

The stent 10 accommodated in the catheter tip K can be cooled by flushing the insertion catheter system with a suitable cooling agent while the catheter tip K is being advanced to keep the temperature of the stent material below the critical transition temperature. Once the catheter tip K with the cooled stent 10 has been advanced to the site of implantation, cooling of the stent 10 should be stopped, as a consequence of which the stent 10 warms up to the body temperature (36° C.) of the patient and the shape memory effect of the stent material is thus activated.

Once the self-expanding property of the individual components of stent 10 have been activated, radial forces are generated which act on the individual components of stent 10, in particular on the positioning arches 15a, 15b, 15c, the retaining arches 16a, 16b, 16c and the auxiliary arches 18a, 18b, 18c of stent 10. Since the respective components of stent 10 are still situated in the catheter tip K, the radial forces developing upon the critical switching temperature being exceeded and acting on the individual components of the stent 10 are still compensated by the wall of the catheter tip K, so that—despite the activation of the shape memory effect—the stent 10 is forcibly kept in its first (collapsed) shape.

Upon the subsequent manipulation of catheter tip K—by the appropriate incremental release of the stent 10—the individual components of stent 10, are then discharged from the catheter tip K. As FIG. 3a shows, the positioning arches 15a, 15b, 15c of stent 10 spread out radially due to the acting radial forces. The expanded positioning arches 15a, 15b, 15c can then be positioned into the pockets T of the native cardiac valve H.

Thereafter—as depicted in FIG. 3b—the remaining components of stent 10 are sequentially released from the catheter tip K. The released remaining components of stent 10, in particular the auxiliary arches 18a, 18b, 18c and the retaining arches 16a, 16b, 16c with the valvular prosthesis 100, then spread out radially and the valvular prosthesis 100 attached to the fastening portions 11 unfolds like an umbrella.

The radial forces acting on both the retaining arches 16a, 16b, 16c and the auxiliary arches 18a, 18b, 18c of the stent 10 as well as the radial forces acting on the upper end region 3 of stent 10, result in the stent 10 being pressed radially against the vascular wall (cf. FIG. 3c). This effects a secure anchoring of stent 10 with the expanded valvular prosthesis 100 at the site of implantation on the one hand and, on the other, a reliable seal of the valvular prosthesis 100 at the lower end 2 of stent 10.

The catheter tip K of the insertion catheter system is then manipulated further to release the eyelets 24 of the stent 10, thereby allowing the upper end region 3 of the stent 10 to expand. In so doing, the valve leaflets of the native cardiac valve H are clamped between respective positioning and retaining arches and the valvular prosthesis 100 disposed on the lower end 2 of stent 10 can spread open.

After the successful implantation of the stent 10 and valvular prosthesis 100, the catheter is then removed from the body of the patient.

The invention is not limited to a stent 10 made from shape memory material which self-expands from its first (collapsed) shape into its second (expanded) shape in response to an external stimulus. Rather, it is also categorically conceivable for the stent 10 to be expanded using a conventional balloon system.

The inventive solution is also not limited to the embodiments as described with reference to the attached drawings. Rather, combinations of the specified individual features are also conceivable.

With respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

LIST OF REFERENCE NUMBERALS 1 endoprosthesis
2 lower end of the stent/endoprosthesis
3 upper end of the stent/endoprosthesis
10 cardiac valve stent/stent
11 fastening portion of the stent
12 fastening holes
13 upper end of the fastening portion
14 lower end of the fastening portion
15a-15c positioning arches
15a', 15a" arms of the first positioning arch
15b', 15b" arms of the second positioning arch 15c', 15c" arms of the third positioning arch
16a-16c retaining arches
16a', 16a" arms of the first retaining arch
16b', 16b" arms of the second retaining arch
16c', 16c" arms of the third retaining arch
17 first connecting web
17d upper end of the first connecting web
17p lower end of the first connecting web
18a-18c auxiliary arches
18a', 18a" arms of the first auxiliary arch
18b', 18b" arms of the second auxiliary arch
18c', 18c" arms of the third auxiliary arch
20 head portion of the positioning arch
21 reference marker
22 connecting portion between the arms of neighboring positioning arches
23 catheter retaining means/catheter retaining head
24 eyelet
25 second connecting web
100 valvular prosthesis
101 thread
102 flap segment of the valvular prosthesis
H native cardiac valve
K catheter tip of an insertion catheter system
L longitudinal direction of the stent
T pocket of the native cardiac valve

The invention claimed is:

1. A method for treating a native cardiac valve, the method comprising:
 positioning a stent within a native cardiac valve, the stent comprising
  a plurality of first arches, each first arch having a closed end portion and an open end portion, the closed end portion pointing in a proximal direction and the open end portion open to a distal end portion of the stent;
  a plurality of second arches, each second arch having a closed end portion and an open end portion, the closed end portion of each second arch pointing in the proximal direction, wherein each second arch is circumferentially aligned with and attached to a respective first arch,
  a plurality of third arches, each third arch having a closed end portion and an open end portion, the closed end portion of each third arch pointing in the proximal direction, and each third arch circumferentially interspaced between two adjacent second arches, and
  a valvular prosthesis attached to the plurality of second arches.

2. The method of claim 1, wherein the native cardiac valve includes a plurality of pockets, and wherein positioning the stent within the native cardiac valve includes positioning the closed end portion of each of the plurality of first arches in a corresponding pocket of the native cardiac valve, and positioning each second arch respective to each first arch radially inward of the corresponding pocket of the native cardiac valve.

3. The method of claim 1, further including releasing the stent; wherein at least one of the plurality of first arches, the plurality of second arches, and the plurality of third arches is configured to expand radially when the stent is released.

4. The method of claim 1, wherein the valvular prosthesis is attached to the plurality of second arches via a plurality of holes defined in each of the plurality of second arches.

5. The method of claim 4, wherein each of the plurality of third arches is connected to two adjacent second arches distally of the plurality of holes in each second arch.

6. The method of claim 1, wherein each first arch attaches to each respective second arch at a respective connecting portion, each connecting portion including an eyelet at a distal end of the stent.

7. The method of claim 6, wherein each third arch is distal from a respective connecting portion.

8. A method for treating a native cardiac valve, the method comprising:
 positioning a stent in a native cardiac valve having a plurality of native valve leaflets, the stent comprising
  a plurality of first arches, each arch having an apex pointing towards a proximal end of the stent and an open end facing a distal end of the stent,
  a plurality of second arches, each second arch having an apex circumferentially aligned with a respective first arch, the apex of each second arch pointing towards the proximal end of the stent,
  a plurality of third arches, each third arch circumferentially interspaced between two adjacent second arches, each third arch having an apex pointing towards the proximal end of the stent, and
  a valvular prosthesis attached to the plurality of second arches;
 wherein positioning the stent in the native cardiac valve includes positioning each of the plurality of first arches in a corresponding pocket of the native cardiac valve.

9. The method of claim 8, wherein positioning the stent in the native cardiac valve includes releasing the plurality of third arches, the plurality of third arches configured to exert a radially outward force.

10. The method of claim 8, wherein each second arch includes a plurality of holes, and wherein the valvular prosthesis is sutured to the plurality of second arches via the plurality of holes.

11. The method of claim 10, wherein each of the plurality of third arches connects a first second arch to an adjacent second arch distally from the plurality of holes of each second arch.

12. The method of claim 8, wherein the stent comprises an equal number of first arches, second arches, and third arches.

13. The method of claim 8, wherein the stent includes a plurality of head portions, each head portion connected to two adjacent first arches, and each head portion including an eyelet.

14. The method of claim 13, further including deploying the stent; wherein the stent is self-expandable, and wherein deploying the stent includes releasing the stent from a collapsed shape via the eyelet of each head portion.

15. The method of claim 8, wherein the apex of each first arch includes a radiopaque marker.

16. A method for treating a native cardiac valve, the method comprising:
 positioning a stent in a native cardiac valve, the stent comprising
  a plurality of first arches,
  a plurality of second arches, each second arch circumferentially aligned with and radially offset from a respective first arch,
  a plurality of third arches, each third arch circumferentially interspaced between two adjacent second arches, and
  a valvular prosthesis attached to the plurality of second arches;
 wherein each of the plurality of first arches, the plurality of second arches, and the plurality of third arches includes an open end portion and a closed end portion, each closed end portion pointing towards a heart chamber when the stent is positioned in the cardiac valve; and wherein positioning the stent in the native cardiac valve includes positioning each of a plurality of leaflets of the native cardiac valve radially between one of the plurality of first arches and each respective second arch.

17. The method of claim 16, wherein the plurality of second arches and the plurality of third arches are uniformly distributed around a circumference of the stent.

18. The method of claim 16, wherein the closed end of each of the plurality of third arches is positioned closer to the heart chamber than the closed end of each of the plurality of first arches.

19. The method of claim 16, wherein the stent includes exactly three first arches, exactly three second arches, and exactly three third arches.

20. The method of claim 16, wherein positioning the stent in the native cardiac valve includes introducing the stent transarterially into a body of a patient using a catheter.

21. The method of claim 16, wherein the stent is self-expanding, and wherein positioning the stent in the native cardiac valve includes releasing the stent from a collapsed shape, the plurality of second arches exerting a radial force against the plurality of leaflets of the native cardiac valve.

\* \* \* \* \*